(12) United States Patent
Pal et al.

(10) Patent No.: US 11,014,915 B2
(45) Date of Patent: May 25, 2021

(54) SELECTIVE ESTROGEN RECEPTOR DEGRADER

(71) Applicant: SUN PHARMA ADVANCED RESEARCH COMPANY LIMITED, Maharashtra (IN)

(72) Inventors: Rajan Kumar Pal, Vadodara (IN); Biswajit Samanta, Vadodara (IN); Jayraj Dilipbhai Aradhye, Vadodara (IN); Sandeep Pankajkumar Pathak, Vadodara (IN); Kaushik Dhanjibhai Prajapati, Vadodara (IN); Bhavesh Mohanbhai Panchal, V.V. Nagar (IN); Trinadha Rao Chitturi, Vadodara (IN)

(73) Assignee: SUN PHARMA ADVANCED RESEARCH COMPANY LIMITED, Maharashtra (IN)

( * ) Notice: Subject to any disclaimer, the term of this patent is extended or adjusted under 35 U.S.C. 154(b) by 0 days.

(21) Appl. No.: 16/936,022

(22) Filed: Jul. 22, 2020

(65) Prior Publication Data

US 2021/0024504 A1 Jan. 28, 2021

(30) Foreign Application Priority Data

Jul. 22, 2019 (IN) .............................. 201921029554

(51) Int. Cl.
*C07D 405/10* (2006.01)
*A61P 35/00* (2006.01)

(52) U.S. Cl.
CPC ............ *C07D 405/10* (2013.01); *A61P 35/00* (2018.01)

(58) Field of Classification Search
None
See application file for complete search history.

(56) References Cited

U.S. PATENT DOCUMENTS

| 5,389,646 A | 2/1995 | Labroo |
| 5,395,842 A | 3/1995 | Labrie et al. |
| 5,407,947 A | 4/1995 | Bryant et al. |
| 6,060,503 A | 5/2000 | Labrie et al. |
| 2004/0034017 A1 | 2/2004 | Kuenzer et al. |

FOREIGN PATENT DOCUMENTS

| EP | 0470310 B1 | 11/1995 |
| WO | WO 99/02512 A1 | 1/1999 |
| WO | WO 2011/156518 A2 | 12/2011 |
| WO | WO 2013/090829 A1 | 6/2013 |
| WO | WO 2013/090836 A1 | 6/2013 |
| WO | WO 2013/090921 A1 | 6/2013 |
| WO | WO 2014/203132 A1 | 12/2014 |
| WO | WO 2014/205136 A1 | 12/2014 |
| WO | WO 2014/205138 A1 | 12/2014 |
| WO | WO 2016/097073 A1 | 6/2016 |
| WO | WO 2016/174551 A1 | 11/2016 |
| WO | WO 2016/189011 A1 | 12/2016 |
| WO | WO 2017/072792 A1 | 5/2017 |

OTHER PUBLICATIONS

Bardia et al., "Emerald: Phase III trial of elacestrant (RAD1901) vs endocrine therapy for previously treated ER+ advanced breast cancer", Future Oncology, vol. 15(28), pp. 3209-3218, published online Aug. 20, 2019.*
Fanning et al., Estrogen receptor alpha somatic mutations Y537S and D538G confer breast cancer endocrine resistance by stabilizing the activating function-2 binding conformation, eLife, Feb. 2, 2016, pp. 1-25.
Wang et al., Brain metastases from breast cancer may respond to endocrine therapy: report of two cases, OncoTargets and Therapy, Feb. 19, 2019, pp. 1389-1393.
Bergen et al., Continued Endocrine Therapy is Associated with Improved Survival in Patients with Breast Cancer Brain Metastases, Precision Medicine and Imaging, Jan. 15, 2019, pp. 2737-2744.
Patel et al., Selective estrogen receptor modulators (SERMs) and selective estrogen receptor degraders (SERDs) in cancer treatment, Pharmacology & Therapeutics, Dec. 28, 2017, pp. 1-24.
Sep. 28, 2020, International Search Report issued for related PCT application No. PCT/IB2020/056914.

* cited by examiner

*Primary Examiner* — Savitha M Rao
*Assistant Examiner* — Gregg Polansky
(74) *Attorney, Agent, or Firm* — Paratus Law Group, PLLC

(57) ABSTRACT

A selective estrogen receptor degrader (SERD), a compound 3-(3,5-difluorophenyl)-2-[4-[(E)-3-[3-(fluoromethyl)azetidin-1-yl]prop-1-enyl]phenyl]-4-methyl-2H-chromen-7-ol, and its S enantiomer, (2S)-3-(3,5-difluorophenyl)-2-[4-[(E)-3-[3-(fluoromethyl)azetidin-1-yl]prop-1-enyl]phenyl]-4-methyl-2H-chromen-7-ol, or pharmaceutically acceptable salts thereof. Also provided are processes for their preparation. Also provided for is the use of these compounds for the treatment of diseases which are related to modulation of estrogen receptors, such as ER-positive breast cancer.

13 Claims, 1 Drawing Sheet

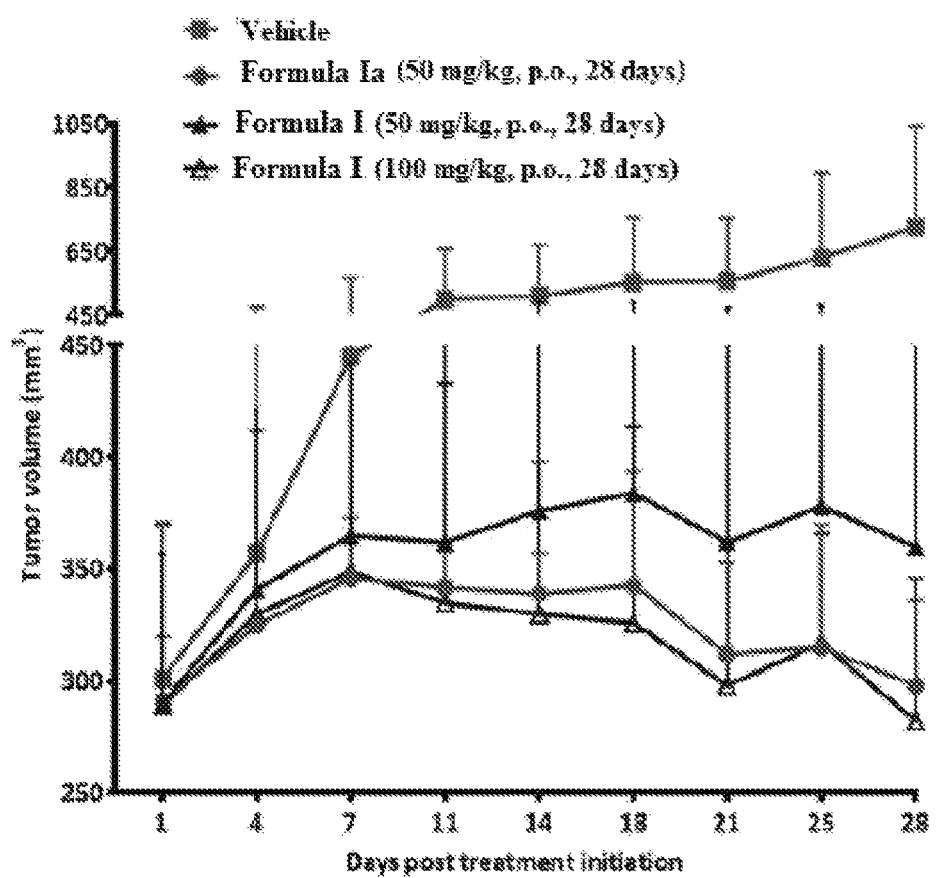

SELECTIVE ESTROGEN RECEPTOR DEGRADER

RELATED APPLICATIONS

This application claims priority to Indian Provisional Patent Application No. IN 201921029554 filed on Jul. 22, 2019, the contents of which are hereby incorporated by reference in their entirety.

FIELD OF THE INVENTION

The present invention relates to a selective estrogen receptor degrader (SERD), a compound 3-(3,5-difluorophenyl)-2-[4-[(E)-3-[3-(fluoromethyl)azetidin-1-yl]prop-1-enyl]phenyl]-4-methyl-2H-chromen-7-ol, and its S enantiomer, (2S)-3-(3,5-difluorophenyl)-2-[4-[(E)-3-[3-(fluoromethyl)azetidin-1-yl]prop-1-enyl]phenyl]-4-methyl-2H-chromen-7-ol, or pharmaceutically acceptable salts thereof. The present invention further provides processes for their preparation. The present disclosure also relates to the use of these compounds and related methods for the treatment of diseases which are related to the modulation of an estrogen receptor (ER), such as ER-positive breast cancer.

BACKGROUND OF THE INVENTION

Endogenous estrogen, 17β-estradiol (E2), shows a wide variety of biological activities in reproductive systems, bone development and turnover, and cardiovascular systems, as well as the central nervous system through interactions with Estrogen Receptors (ERs). ERs have been found to have two isoforms, ER-α and ER-β. The link between estrogen and breast cancer growth and development has been well established.

A number of strategies to inhibit the action of endogenous estrogen in estrogen receptor positive breast cancer are in practice. These include: selective ER modulators (SERMs) such as tamoxifen, which act as selective tissue-specific antagonist of ERs in the breast; selective ER degraders (SERD) such as fulvestrant, which promote ER turnover; and aromatase inhibitors (AI) such as exemestane (steroidal), anastrozole and letrozole (nonsteroidal) which inhibit estrogen biosynthesis and are primarily used for postmenopausal women with ER-positive breast cancer. Unfortunately, many women with breast cancer initially respond well to tamoxifen or AI therapy but develop resistance over a period of time during treatment. In the resistant form of breast cancer there is evidence that pro-growth signaling pathways downstream of estrogen receptors still play a significant role. Recently, there has been increasing clinical evidence that following treatment with AIs, resistance develop due to mutations in the ligand-binding domain of ER-α, rendering it constitutively active even in the absence of ligand, thus leading to resistance.

Fanning reported that the most prevalent ER-α point mutations were Y537S and D538G, while several others were identified at significantly reduced frequencies. Importantly, breast cancer cell-based studies revealed that the Y537S and D538G mutations conferred hormone-independent activation of ER-α and reduced the inhibitory potency and efficacy of clinically prescribed SERMs and SERDs (Fanning et al. eLife 2016; 5:e12792).

Currently, fulvestrant is considered as a first-in-class SERD. Unfortunately, significant pharmaceutical liabilities of fulvestrant, namely its requirement of an intramuscular injection of a large volume, its poor solubility, and its lack of oral bioavailability limit its widespread use. Therefore, the development of an orally bio-available ER-antagonist, especially one with ER degrading properties, would be beneficial to patients who have developed resistance to currently available therapies targeting ER activity. Several novel SERDs have been recently developed which are currently in different phases of clinical trials, for example, SAR-439859 (Phase II), LSZ-102(Phase I), AZD-9496 (Phase II), GDC-810 (currently discontinued), GDC-927 (currently discontinued), and others. Many non-steroidal ER antagonists are reported in prior art. For instance, the U.S. Pat. Nos. 5,395,842 and 6,060,503 disclose anti-estrogenic compounds and compositions.

U.S. Pat. Nos. 5,389,646, 5,407,947; European Patent No. EP470310B1 and WIPO Publication No. WO9902512A1 disclose benzopyran compounds useful for treatment or prevention of conditions modulated through the estrogen receptor.

United States Patent Application Publication No. US2004034017 (assigned to Schering Aktiengesellschaft) discloses 4-fluoroalkyl-2H-benzopyran derivatives as antiestrogens.

WIPO Publication Nos. WO2011156518A2 and WO2013090829A1 (both assigned to Aragon Pharmaceuticals Inc.) disclose a large genus of 2H-chromene derivatives as estrogen receptor modulators.

WO2013090836A1 (Assigned to Aragon pharmaceuticals, Inc.) discloses 2H-chromene derivatives having a fluorinated azetidine or pyrrolidine ring in the side chain as estrogen receptor modulators/ER degraders.

WO2014205136A1 and WO2014205138A1 (both assigned to Seragon pharmaceuticals, Inc.) disclose 4-methyl-2H-chromene derivatives and stereoisomers thereof having a fluoromethylazetidine group in the side chain as estrogen receptor modulators/ER degraders.

WO2016097073A1 (assigned to F. Hoffmann-La Roche AG/Genentech, Inc.) discloses 2H-chromene derivatives having a fluoromethylazetidine group or a fluoromethylpyrrolidine group in the side chain as estrogen receptor modulators/ER degraders.

WO2016189011A1 (assigned to F. Hoffmann-La Roche AG/Genentech, Inc.) discloses 2H-chromene derivatives having a fluoromethylazetidine or a pyrrolidine group in the side chain as estrogen receptor modulators/ER degraders.

WO2013090921A1 and WO2014203132A1 (both assigned to Olema Pharmaceuticals, Inc.) disclose benzopyran derivatives having methylpyrrolidine in the side chain as antiestrogens.

WO2016174551A1 (assigned to Pfizer Inc.) discloses 2H-chromene derivatives having N-alkylated azetidine in the side chain as anti-estrogens.

SUMMARY OF THE INVENTION

The present invention provides a compound 3-(3,5-difluorophenyl)-2-[4-[(E)-3-[3-(fluoromethyl)azetidin-1-yl]prop-1-enyl]phenyl]-4-methyl-2H-chromen-7-ol represented by Formula I:

Formula I

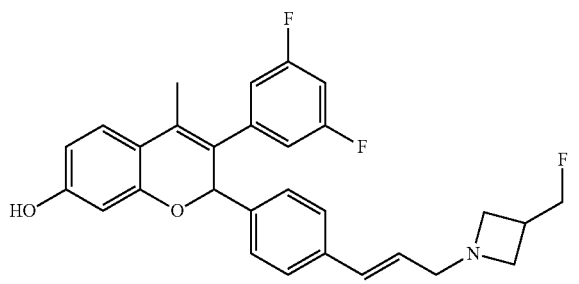

or a pharmaceutically acceptable salt thereof.

The present invention also provides a compound (2S)-3-(3,5-difluorophenyl)-2-[4-[(E)-3-[3-(fluoromethyl)azetidin-1-yl]prop-1-enyl]phenyl]-4-methyl-2H-chromen-7-ol represented by Formula Ia:

Formula Ia

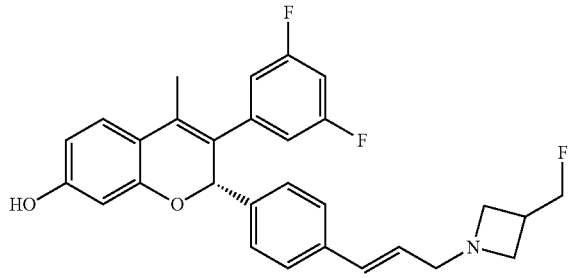

or a pharmaceutically acceptable salt thereof.

The compounds of present invention are selective estrogen receptor degraders and can be used for the treatment of diseases which are related to the modulation of ER.

Glossary

"Pharmaceutically acceptable salt" as used herein includes one or more types of acid addition salts formed with either organic or inorganic acids. Suitable pharmaceutically acceptable salts of the compounds disclosed herein include, but are not limited to, acid addition salts which may be salts of inorganic acids such as hydrochloric acid, hydrobromic acid, and phosphoric acid, or of organic acids such as, for example, acetic acid, benzenesulfonic acid, methanesulfonic acid, benzoic acid, citric acid, glycolic acid, lactic acid, fumaric acid, succinic acid, adipic acid, pimelic acid, suberic acid, azelaic acid, malic acid, tartaric acid, and amino acids such as glutamic acid or aspartic acid.

The term "effective amount" as used herein refers to an amount of the compound which is sufficient, upon single or multiple dose administration(s) to a subject, in curing, alleviating, relieving or partially addressing the clinical manifestation of a given disease or state and its complications beyond that expected in the absence of such treatment. Thus, the result can be reduction and/or alleviation of the signs, symptoms, or causes of a disease, or any other desired alteration of a biological system. It is understood that "a therapeutically effective amount" can vary from subject to subject depending on age, weight, general condition of the subject, the condition being treated, the severity of the condition being treated, and the judgment of the prescribing physician.

The term "treating" or "treatment" as used herein refer to completely or partially curing, alleviating, ameliorating, improving, relieving, delaying onset of, inhibiting progression of, reducing severity of, and/or reducing incidence of one or more symptoms or features of a particular disease, disorder, and/or condition.

A human in need of the methods or compounds or treatments disclosed herein are those who are either suffering from the particular disease, disorder, and/or conditions described herein or at a recognized risk, such as by medical diagnosis, of developing that particular disease, disorder, and/or condition.

BRIEF DESCRIPTION OF DRAWINGS

FIG. 1. In-vivo efficacy of a compound of Formula I and a compound of Formula Ia in MCF7-Y537S mice xenografts.

DETAILED DESCRIPTION OF THE INVENTION

Previously the present applicant had filed a patent application published as WIPO Publication No. WO2017072792A1 covering 2H-chromene derivatives having a heterocyclic ring in the side chain as ER antagonists/degraders. The present inventors, in a quest to further develop a better orally bio-available ER-antagonist especially with ER degrading properties, surprisingly found that the compound of Formula I having a 7-hydroxy chromene moiety and an azetidine ring side chain in the structure exhibits a significant degradation of estrogen receptors. It was further found that the S-stereoisomer of the compound of Formula I was significantly more potent than the R-isomer. Moreover, it was surprisingly found that the S-isomer of the compound of Formula I exhibits pharmacokinetic properties which make it much more efficacious over the R-isomer. Accordingly, in one aspect, the present invention provides a compound 3-(3,5-difluorophenyl)-2-[4-[(E)-3-[3-(fluoromethyl)azetidin-1-yl]prop-1-enyl]phenyl]-4-methyl-2H-chromen-7-ol represented by Formula I:

Formula I

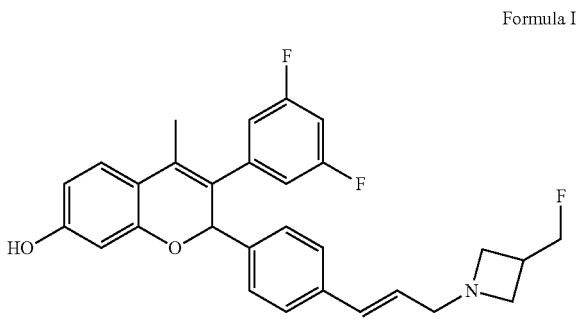 [SMILES: CC1=C(c2cc(F)cc(F)c2)C(c2ccc(/C=C/CN3CC(CF)C3)cc2)Oc2cc(O)ccc21]

or a pharmaceutically acceptable salt thereof.

When the present inventors carried out the chiral resolution of the compound of Formula I into its enantiomers, the 'S' enantiomer was surprisingly found to be significantly superior to the 'R' enantiomer in terms of both its in-vitro potency in an MCF-7 growth inhibition assay/ER-α degradation assay as well as in its pharmacokinetic profile. Accordingly in a second aspect, the present invention provides a compound (2S)-3-(3,5-difluorophenyl)-2-[4-[(E)-3-

[3-(fluoromethyl)azetidin-1-yl]prop-1-enyl]phenyl]-4-methyl-2H-chromen-7-ol represented by Formula Ia:

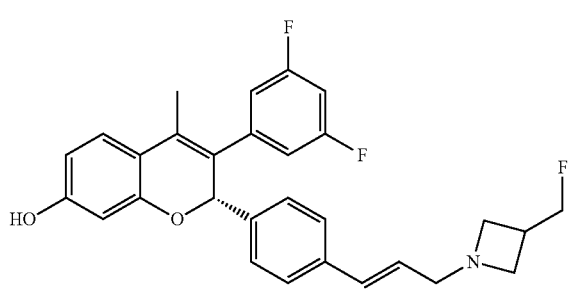

Formula Ia and/or a pharmaceutically acceptable salt thereof.

One aspect of the present invention is therefore a composition in which at least 75% of the total amount of enantiomers of Formula I that are present in the composition are the S enantiomer. In certain embodiments, this percentage may be at least 85%, at least 90%, at least 95%, at least 99% and 100% of the enantiomers of Formula I that are present are the S enantiomer. In other embodiments, the composition does not contain the R enantiomer of Formula I.

In another aspect, the present invention provides a compound of Formula Ia or a pharmaceutically acceptable salt thereof, which is substantially free of compound of Formula Ib

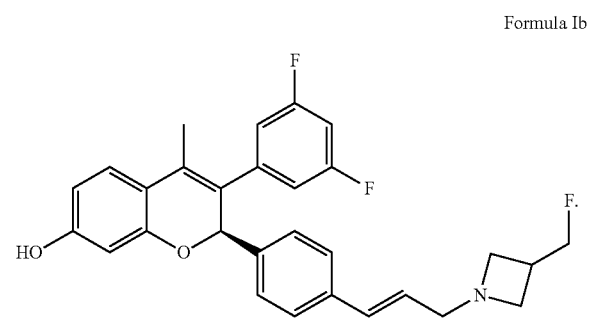 [SMILES: CC1=C(c2cc(F)cc(F)c2)[C@@H](c2ccc(/C=C/CN3CC(CF)C3)cc2)Oc2cc(O)ccc21]

Formula Ib

The term "substantially free of compound of Formula Ib" refers to content of compound of Formula Ib which is less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, less than 0.1%, less than 0.09%, less than 0.05% or less than 0.01% w/w with respect to compound of Formula Ia or the compound of Formula Ib is absent.

Thus in one embodiment, the present invention provides a compound of Formula Ia or a pharmaceutically acceptable salt thereof, wherein the content of compound of Formula Ib is less than 25%, less than 20%, less than 15%, less than 10%, less than 5%, less than 1%, less than 0.5%, less than 0.1%, less than 0.05%, less than 0.01% w/w or absent with respect to the compound of Formula Ia.

In another embodiment, the present invention provides a compound of Formula Ia or a pharmaceutically acceptable salt thereof, wherein the enantiomeric ratio of the compound of Formula Ia to the compound of Formula Ib is greater than 75:25, greater than 80:20, greater than 85:15, greater than 90:10, greater than 95:5, greater than 96:4, greater than 97:3, greater than 98:2, greater than 99:1 or is 100:0.

In another embodiment, the present invention provides a compound of Formula Ia or a pharmaceutically acceptable salt thereof, wherein the enantiomeric ratio of the compound of Formula Ia to the compound of Formula Ib is greater than 80:20. In another embodiment, the enantiomeric ratio of the compound of Formula Ia is greater than 85:15. In another embodiment, the enantiomeric ratio of the compound of Formula Ia is greater than 90:10. In another embodiment, the enantiomeric ratio of the compound of Formula Ia is greater than 95:5. In another embodiment, the enantiomeric ratio of the compound of Formula Ia is greater than 96:4. In another embodiment, the enantiomeric ratio of the compound of Formula Ia is greater than 97:3. In another embodiment, the enantiomeric ratio of the compound of Formula Ia is greater than 98:2. In another embodiment, the enantiomeric ratio of the compound of Formula Ia is greater than 99:1. In another embodiment, the enantiomeric ratio of the compound of Formula Ia is 100:0 i.e. the compound of Formula Ib (R enantiomer) is absent.

The present invention also includes the prodrugs or deuterated derivatives of the compound of Formula I or Formula Ia.

The compounds of the present invention as described herein are ER-antagonists especially with ER degrading properties, and therefore are believed to be useful as medicaments, particularly for the treatment of diseases that are ER dependent or ER mediated, such as cancer, selected from, but not limited to breast cancer, ovarian cancer, brain cancer and endometrial cancer.

Given the central role of ER-α in breast cancer development and progression, the compounds of the present invention can be useful in the treatment of breast cancer, either alone or in combination with other agent, including but not limited to: aromatase inhibitors (such as anastrozole, letrozole, and the like), SERMs (such as tamoxifen, raloxifene, and the like), antiestrogens (such as fulvestrant and the like), luteinizing hormone-releasing hormone (LH-RH) agonists (such as leuprolide and the like), CDK4/6 inhibitors (such as palbociclib and the like) or other chemotherapeutic agents including anthracylines, platins, nitrogen mustard alkylating agents, and the like.

Thus, in another aspect, the present invention provides a method of treatment of an ER dependent or ER mediated disease or condition in a human being in need thereof, comprising administering thereto an effective amount of a compound of Formula I or a pharmaceutically acceptable salt thereof.

In another embodiment, the present invention provides a method of treatment of an ER dependent or ER mediated disease or condition in a human being in need thereof, comprising administering thereto an effective amount of a compound of Formula Ia or a pharmaceutically acceptable salt thereof.

In another embodiment, the present invention provides a method of treatment of cancer selected from breast cancer, endometrial cancer, brain cancer and ovary cancer in a human being in need thereof, comprising administering thereto an effective amount of a compound of Formula I or a pharmaceutically acceptable salt thereof.

In another embodiment, the present invention provides a method of treatment of cancer selected from breast cancer, endometrial cancer, brain cancer and ovary cancer in a human being in need thereof, comprising administering thereto an effective amount of a compound of Formula Ia or a pharmaceutically acceptable salt thereof.

In another embodiment, the present invention provides a method of treatment of breast cancer, comprising administering an effective amount of a compound of Formula I or compound of Formula Ia or a pharmaceutically acceptable salt thereof.

Pharmaceutical Composition

The compounds disclosed herein may be formulated into a composition that additionally comprises suitable pharmaceutically acceptable carriers, including excipients and other compounds that facilitate administration of the compound to a subject. The pharmaceutical compositions of the present invention may be formulated in a conventional manner using one or more pharmaceutically acceptable excipients. The pharmaceutically acceptable excipients may include items such as diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents, and the like. The compounds of the present invention may be formulated in the form of pills, tablets, coated tablets, capsules, powder, granules, pellets, patches, implants, films, liquids, semi-solids, gels, aerosols, emulsions, elixirs, and the like. Such pharmaceutical compositions and the processes for preparing the same are described, for example, in Remington: The Science and Practice of Pharmacy (D. B. Troy, Editor, 21st Edition, Lippincott, Williams & Wilkins, 2006), the contents of which are incorporated herein by reference in their entirety. In certain embodiments, the compounds and compositions described herein may be administered orally, parenterally, intramuscularly, transdermally or intravenously.

Thus, in one embodiment, the present invention provides a pharmaceutical composition comprising a compound of Formula I or a compound of Formula Ia, or a pharmaceutically acceptable salt thereof, with a pharmaceutically acceptable carrier, diluent, or excipient.

Suitable doses of the compounds for use in treating the diseases as described herein can be determined by those skilled in the relevant art. Therapeutic doses are generally identified through a dose ranging study in humans based on preliminary evidence derived from animal studies. Doses must be sufficient to result in a desired therapeutic benefit without causing unwanted side effects. The mode of administration, dosage forms, and suitable pharmaceutical excipients can also be understood and adjusted by those skilled in the art.

The present invention is further illustrated in detail with reference to the following examples. It should be understood that the examples herein are merely illustrative, and do not limit the scope of the present disclosure or the claims appended hereto.

Process of Preparation

A compound of Formula I, a compound of Formula Ia, and their closely related analogues were prepared as described below. All solvents and reagents were used as obtained from commercial sources unless otherwise indicated. $^1$H-NMR spectra were recorded with a Bruker® spectrometer operating at 500 MHz in deuterated DMSO.

The compound of Formula I or the compound of Formula Ia can be converted into their salts by methods known in the art, including, for example, dissolving a compound of Formula I or Formula Ia in a suitable solvent and treating it with an appropriate acid.

Example 1: Preparation of 3-(3,5-difluorophenyl)-2-{4-[(E)-3-(3-fluoromethyl azetidin-1-yl)propenyl]phenyl}-4-methyl-2H-chromen-7-ol (Compound of Formula I)

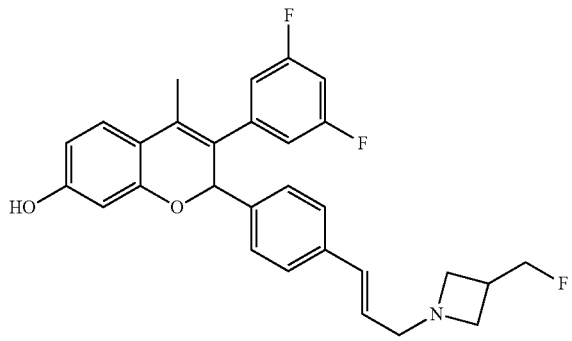

Formula I

Step-I: Preparation of 2-(3,5-difluorophenyl)-1-(2,4-dihydroxyphenyl)ethanone

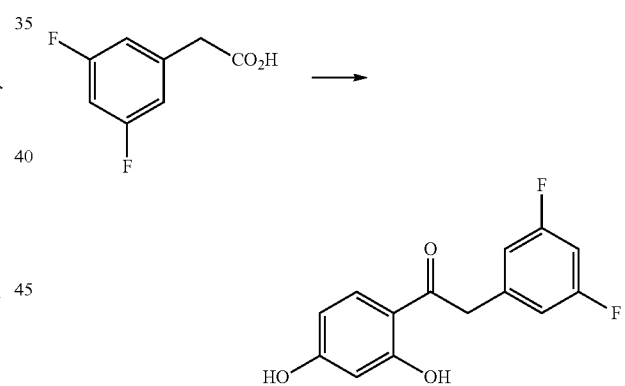

Oxalyl chloride (5.98 mL, 0.070 mol) was added dropwise to a stirred solution of 3,5-difluorophenylacetic acid (10 g, 0.058 mol) and N,N-dimethylformamide (0.5 mL) in dichloromethane (100 mL) at room temperature and was stirred at room temperature for 30 min. The reaction mixture was concentrated under reduced pressure at 30-35° C. and then dissolved in dichloromethane (20 mL). The resultant solution was added to a stirred solution of resorcinol (9.58 g, 0.087 mol) and aluminium chloride (11.60 g, 0.087 mol) in dichloromethane (80 mL) at 0-5° C. and was stirred at room temperature for 16 hours. The reaction was slowly quenched with 2N hydrochloric acid solution (120 mL) at 0-5° C. and stirred for 1 hr at same temperature. The solid was filtered and successively washed with water and n-hexane. The resulting solid was dried under vacuum to give 2-(3,5-difluorophenyl)-1-(2,4-dihydroxyphenyl)ethanone.

Step-II: Preparation of 2-(3,5-difluorophenyl)-1-[2-hydroxy-4-(tetra hydropyran-2-yloxy)phenyl]ethanone

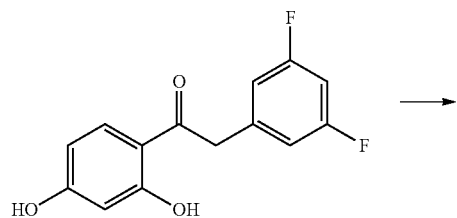

3,4-Dihydro-2H-pyran (45.58 mL, 0.50 mol) was added to a stirred solution of 2-(3,5-difluorophenyl)-1-(2,4-dihydroxyphenyl)ethanone (44.0 g, 0.167 mol) and pyridinium p-toluene sulfonate (6.28 g, 0.025 mol) in dichloromethane (880 mL) at room temperature. The reaction mixture was stirred at room temperature for 2 hours and quenched with an aqueous saturated solution of sodium bicarbonate. The organic layer was separated and the aqueous layer was again extracted with dichloromethane. The combined organic layer was dried over anhydrous sodium sulfate and concentrated under reduced pressure to give crude mass which was stirred in a mixture of n-hexane:ethyl acetate (95:5) at room temperature and filtered to give 2-(3,5-difluorophenyl)-1-[2-hydroxy-4-(tetrahydropyran-2-yloxy)-phenyl]ethanone.

Step-III: Preparation of 3-(3,5-difluorophenyl)-2-(4-iodophenyl)-7-(tetrahydropyran-2-yloxy)chroman-4-one

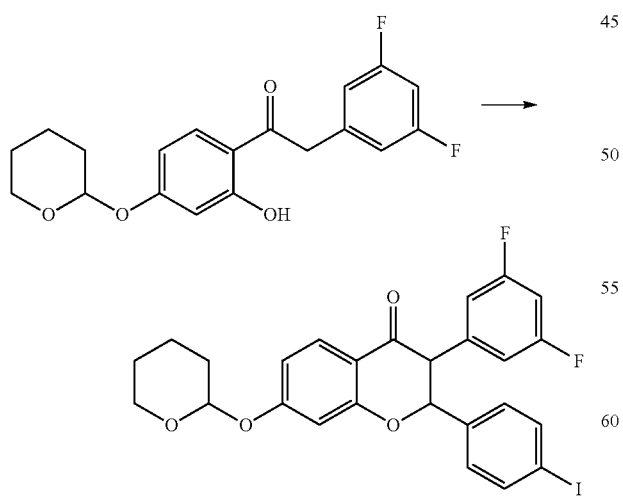

1,8-Diazabicyclo(5.4.0)undec-7-ene (DBU, 0.055 g, 0.00036 mol) was added to a stirred slurry of 2-(3,5-difluorophenyl)-1-[2-hydroxy-4-(tetrahydropyran-2-yloxy)-phenyl]ethanone (0.5 g, 0.0014 mol), 4-iodo benzaldehyde (0.37 g, 0.0016 mol) and piperidine (0.03 g, 0.00036 mol) in isopropyl alcohol (10 mL). The reaction mixture was heated to 90-95° C. for 3 hours. The solvent was removed under reduced pressure to give 3-(3,5-difluorophenyl)-2-(4-iodophenyl)-7-(tetrahydropyran-2-yloxy)chroman-4-one.

Step-IV: Preparation of 3-(3,5-difluorophenyl)-2-(4-iodophenyl)-4-methyl-7-(tetrahydropyran-2-yloxy)-chroman-4-ol

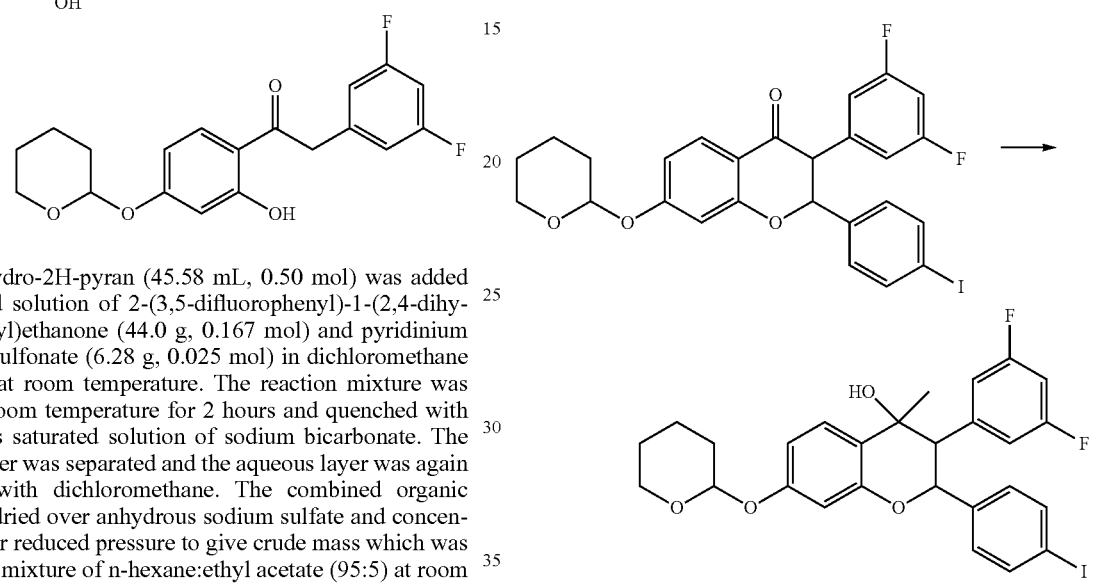

Methyl magnesium chloride (3M) in tetrahydrofuran (THF, 1.6 mL) was added to a stirred solution of 3-(3,5-difluorophenyl)-2-(4-iodophenyl)-7-(tetrahydropyran-2-yloxy)-chroman-4-one (0.8 g, 0.0014 mol) in anhydrous THF (12 mL) at 20-25° C. and stirred for 1 hour. The reaction mixture was quenched with an aqueous saturated ammonium chloride solution at 0-5° C. followed by water. The organic layer was separated and the aqueous layer was again extracted with ethyl acetate. The combined organic layer was dried over anhydrous sodium sulfate and solvent was removed under vacuum to give the title compound.

Step-V: Preparation of 3-(3,5-difluorophenyl)-2-(4-iodophenyl)-4-methyl-2H-chromen-7-ol

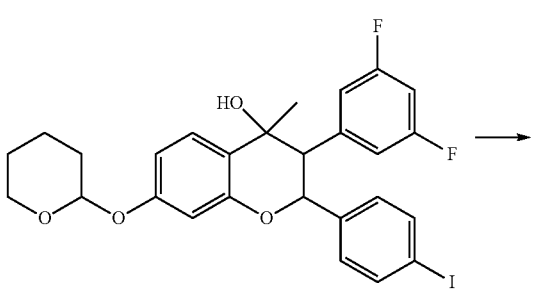

-continued

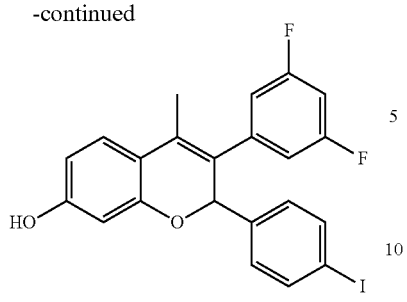

A solution of concentrated sulfuric acid (0.22 mL, 0.0042 mol) in methanol (2 mL) was added to a stirred solution of 3-(3,5-difluorophenyl)-2-(4-iodophenyl)-4-methyl-7-(tetrahydropyran-2-yloxy)-chroman-4-ol (0.8 g, 0.0014 mol) in methanol (10 mL) and heated at 65-70° C. for 3 hours. The reaction mixture was cooled to 0-5° C. Saturated sodium bicarbonate solution was added to the above reaction mixture and was extracted with ethyl acetate. The combined organic layer was dried over anhydrous sodium sulfate and solvent was removed under vacuum to give a crude mass which was purified by column chromatography (silica gel, toluene:ethyl acetate (97:3)) to give the title compound.

Step-VI: Preparation of 3-(3,5-difluorophenyl)-2-(4-iodophenyl)-4-methyl-7-(tetrahydrohydropyran-2-yloxy)-2H-chromene

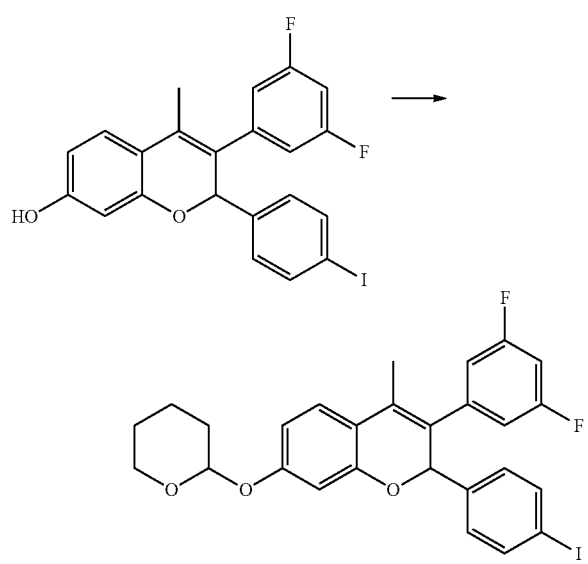

3,4-Dihydro-2H-pyran (10.34 mL, 0.113 mol) was added to a stirred solution of 3-(3,5-difluorophenyl)-2-(4-iodophenyl)-4-methyl-2H-chromen-7-ol (18 g, 0.038 mol) and pyridinium p-toluenesulfonate (1.42 g, 0.0057 mol) in dichloromethane (200 mL) at room temperature and was stirred for 16 hrs. The reaction mixture was quenched with a saturated solution of sodium bicarbonate. The organic layer was separated and the aqueous layer was extracted with dichloromethane. The combined organic layer was dried over anhydrous sodium sulfate and solvent was removed under vacuum to give a crude mass which was purified by column chromatography (silica gel, toluene) to give the title compound.

Step-VII: Preparation of (E)-3-{4-[3-(3,5-difluorophenyl)-4-methyl-7-(tetrahydropyran-2-yloxy)-2H-chromen-2-yl]phenyl}acrylic acid ethyl ester

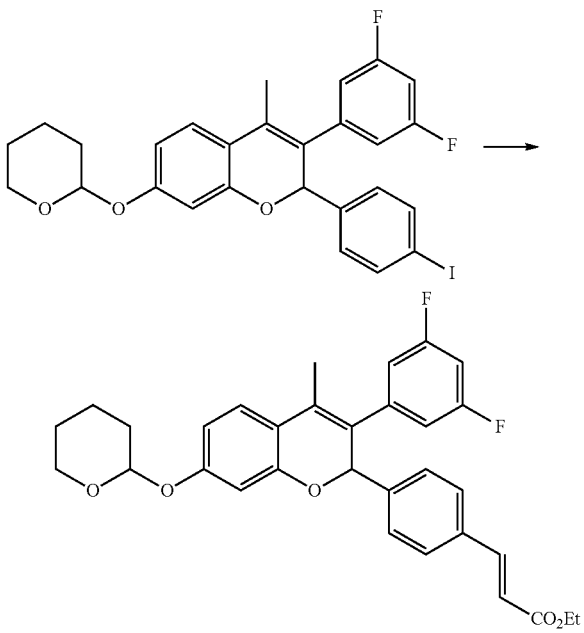

Ethyl acrylate (0.23 g, 0.0022 mol) was added to a stirred solution of 3-(3,5-difluorophenyl)-2-(4-iodophenyl)-4-methyl-7-(tetrahydrohydropyran-2-yloxy)-2H-chromene (0.25 g, 0.00045 mol) and triethylamine (0.37 mL, 0.0027 mol) in N-methyl-2-pyrrolidone (2 mL) followed by addition of Pd(PPh$_3$)$_2$Cl$_2$ (0.003 g, 0.0000044 mol) at room temperature. The resultant reaction mixture was heated at 95° C. for 1 hour. Water was added to the reaction mixture and the product was extracted with ethyl acetate. The combined organic layer was dried over anhydrous sodium sulfate and solvent was removed under vacuum to give a crude mass which was purified by column chromatography (silica gel, n-hexane:ethyl acetate (85:15)) to give the title compound.

Step-VIII: Preparation of (E)-3-{4-[3-(3,5-Difluorophenyl)-4-methyl-7-(tetrahydropyran-2-yloxy)-2H-chromen-2-yl]-phenyl}prop-2-en-1-ol

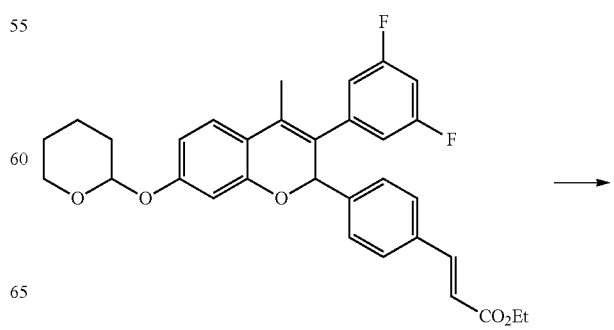

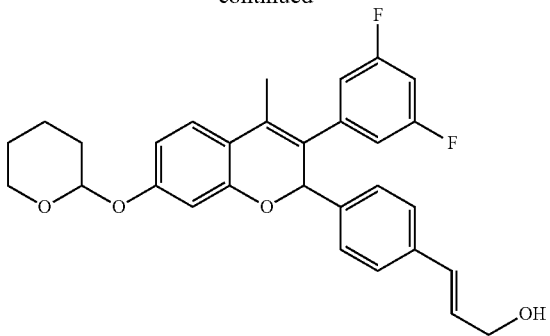

Diisobutylaluminium hydride (20%) solution in toluene (0.56 mL, 0.00079 mol) was added to a stirred solution of (E)-3-{4-[3-(3,5-difluorophenyl)-4-methyl-7-(tetrahydropyran-2-yloxy)-2H-chromen-2-yl]-phenyl}acrylic acid ethyl ester (0.14 g, 0.00026 mol) in toluene (5.6 mL) at −30° C. and was stirred for 45 min. at −20 to −25° C. Methanol (0.5 mL) and sodium potassium tartrate (20%) solution (5 mL) was dropwise added at −20° C. The reaction mixture was brought to room temperature and was treated with water at room temperature. The organic layer was separated and the aqueous layer was extracted with dichloromethane. The combined organic layer was dried over anhydrous sodium sulfate and solvent was removed under reduced pressure to give a crude mass which was purified by column chromatography (silica gel, n-hexane:ethyl acetate (60:40)) to give the title compound.

Step-IX: 1-((E)-3-{4-[3-(3,5-difluorophenyl)-4-methyl-7-(tetrahydropyran-2-yloy)-2H-chromen-2-yl]-phenyl}allyl)-3-fluoromethylazetidine Iodine (1.02 g, 0.0041 mol) was added portion wise to a stirred solution of triphenyl phosphine (1.07 g, 0.0041 mol) and imidazole (0.31 g, 0.0045 mol) in dichloromethane (10 mL) at 0-5° C. The reaction mixture was stirred at 0-5° C. for 30 min. A solution of (E)-3-{4-[3-(3,5-difluorophenyl)-4-methyl-7-(tetrahydropyran-2-yloxy)-2H-chromen-2-yl]phenyl}prop-2-en-1-ol (1.0 g, 0.0020 mol) in dichloromethane (10 mL) was added at 0-5° C. to this reaction mixture and stirred for 20 minutes. It was slowly poured into a cold solution of sodium bicarbonate and extracted with dichloromethane. The combined organic layer was successively washed with an aqueous solution of sodium metabisulphite and brine solution. The organic layer was dried over anhydrous sodium sulfate and solvent was removed under vacuum to give a crude mass. A mixture of n-hexane:ethyl acetate (9:1)(20 mL) was added to the above crude mass and stirred for 30 min at room temperature. Finally it was filtered and the filtrate was concentrated under reduced pressure at 35-38° C. to give a crude mass, which was again stirred in a mixture of n-hexane:ethyl acetate (9:1) (10 mL) for 30 min. It was again filtered and the filtrate was concentrated under reduced pressure at 35-38° C. to give 3-(3,5-difluorophenyl)-2-[4-((E)-3-iodopropenyl)phenyl]-4-methyl-7-(tetrahydro pyran-2-yloxy)-2H-chromene.

Triethylamine (0.56 mL, 0.004 mol) was added to a stirred solution of 3-fluoromethyl azetidine hydrochloride (0.38 g, 0.003 mol) in acetonitrile (10 mL). The reaction mixture was stirred for 30 minutes at room temperature. A solution of 3-(3,5-difluorophenyl)-2-[4-((E)-3-iodopropenyl)phenyl]-4-methyl-7-(tetrahydro-pyran-2-yloxy)-2H-chromene (1.2 g, 0.002 mol) in acetonitrile (10 mL) was added to the reaction mixture at room temperature and stirring was continued for 45 minutes. Water was added to the reaction mixture and was extracted with ethyl acetate. The organic layer was separated, dried over anhydrous sodium sulfate and solvent was removed under reduced pressure to give a crude mass which was purified by column chromatography (silica gel, dichloromethane:methanol (97:3)) to give the title compound.

Step-X: Preparation of 3-(3,5-difluorophenyl)-2-{4-[(E)-3-(3-fluoromethyl azetidin-1-yl)propenyl]phenyl}-4-methyl-2H-chromen-7-ol (Formula I)

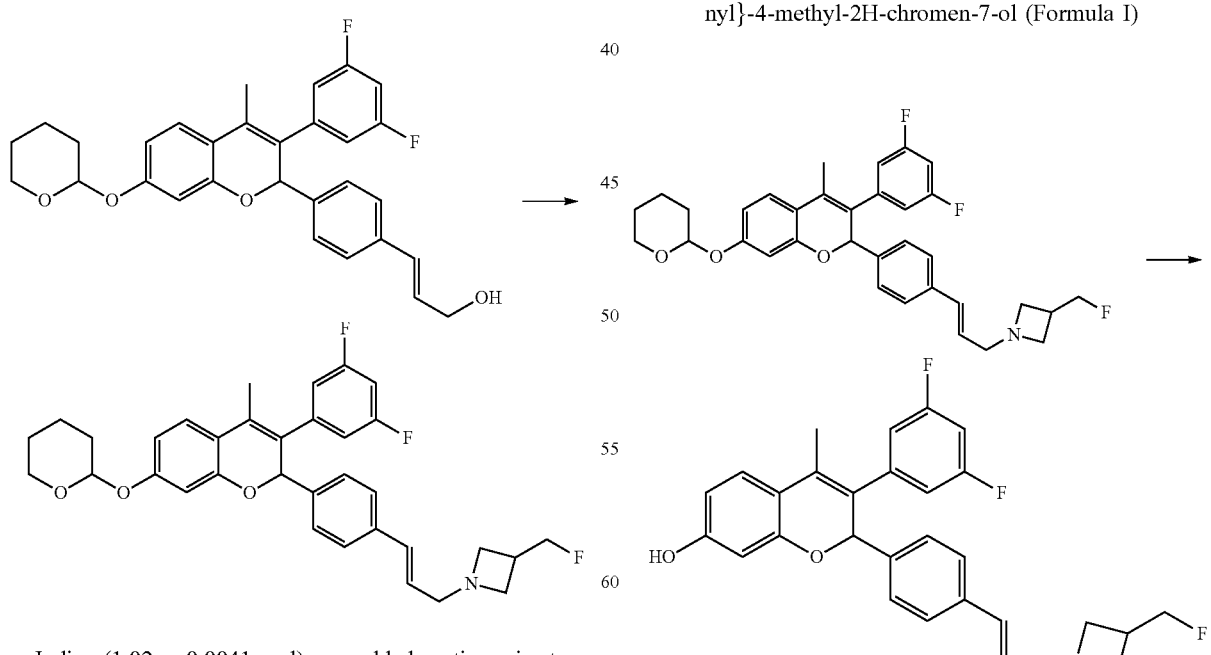

Formula I

A solution of sulfuric acid (0.75 mL, 0.014 mol) in methanol (70 mL) was added to a stirred solution of 1-((E)-3-{4-[3-(3,5-difluorophenyl)-4-methyl-7-(tetrahydropyran-2-yloxy)-2H-chromen-2-yl]-phenyl}allyl)-3-fluoromethyl azetidine (7.6 g, 0.014 mol) in methanol (20 mL) at 0-5° C. The reaction mixture was allowed to stir for 30 minutes at room temperature. A saturated solution of sodium bicarbonate and water were added at 0-5° C. and was extracted with dichloromethane. The combined organic layer was dried over anhydrous sodium sulfate and concentrated under reduced pressure to get residue which was purified by column chromatography (silica gel, dichloromethane:methanol (90:10)) to give the title compound.

Example 2: Preparation of (2S)-3-(3,5-difluorophenyl)-2-[4-[(E)-3-[3-(fluoromethyl)azetidin-1-yl]prop-1-enyl]phenyl]-4-methyl-2H-chromen-7-ol (Compound of Formula Ia) and (2R)-3-(3,5-difluorophenyl)-2-[4-[(E)-3-[3-(fluoromethyl)azetidin-1-yl]prop-1-enyl]phenyl]-4-methyl-2H-chromen-7-ol (Compound of Formula Ib)

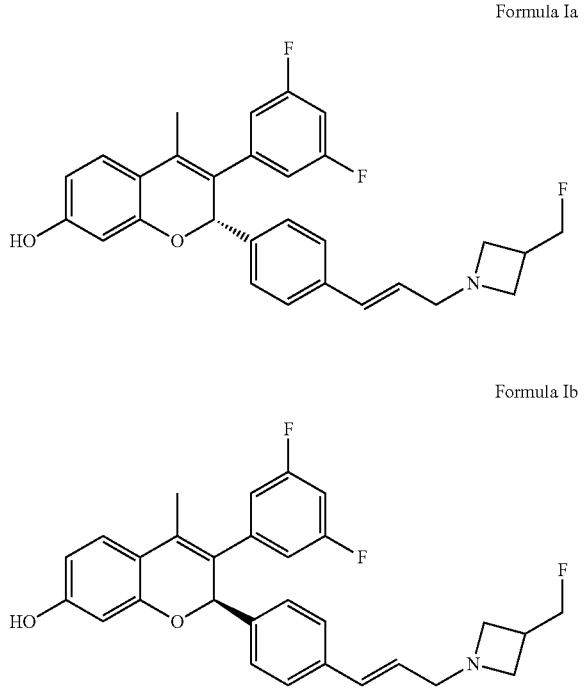

Formula Ia

Formula Ib

The enantiomers from the racemic mixture of example 1 were separated by chiral HPLC (Column: Chiralcel® OD-H (250×30 mm, 5µ); mobile phase-n-hexane:ethanol:diethyl amine 900:100:1) wherein R enantiomer (Compound of Formula Ib) was eluted first followed by desired S enantiomer (Compound of Formula Ia). Further the specific optical rotation (SOR) of compound of Formula Ia was determined by using following test conditions:

Concentration: 1% w/v in acetone;
Temperature: 25° C.;
Source of light: Sodium lamp (D line);
SOR of Compound of Formula Ia: $[\alpha]_D^{25}$=+224.40°

The chiral purity of compound of Formula Ia was determined by HPLC as per following analytical conditions:

Column: CHIRALCEL® OD-3 (250×4.6) mm 3 µm

Mobile phase: n-hexane/ethanol/diethylamine (90/10/0.1, v/v/v)

Flow rate: 1.0 mL/min; Column Temperature: 25° C.: detector: UV:230 nm:

Sample concentration: 0.5 mg/mL

Diluent: Mobile phase.

Chiral Purity of compound of Formula Ia=99.69:0.31 (S:R); Relative retention time (RRT) with respect to compound of Formula Ib=About 1.1

Example 3: Preparation of 3-(3,5-difluorophenyl)-2-[4-[(E)-3-[3-(fluoromethyl)azetidin-1-yl]prop-1-enyl]phenyl]-4-methyl-2H-chromen-6-ol (Compound 2)

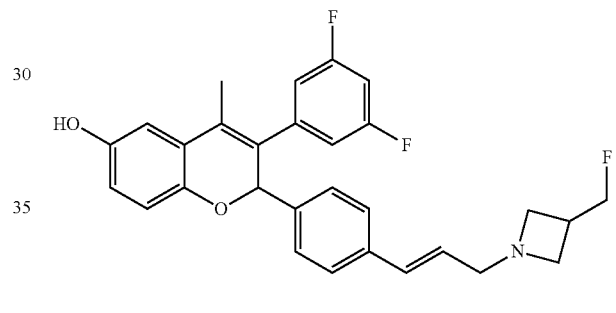

Compound 2

Racemic compound 2 was prepared by following an analogous process of Example 1 (step III-step X) wherein 2-(3,5-difluorophenyl)-1-(2-hydroxy-5-tetrahydropyran-2-yloxy-phenyl)ethanone was used instead of 2-(3,5-difluoro phenyl)-1-[2-hydroxy-4-(tetrahydropyran-2-yloxy)-phenyl] ethanone in step III.

Example 4: Preparation of 3-(3,5-difluorophenyl)-2-{4-[(E)-3-(4-fluoromethylpiperidin-1-yl)propenyl] phenyl}-4-methyl-2H-chromen-7-ol (Compound 3)

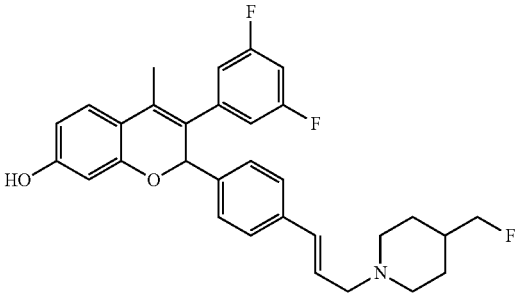

Compound 3

Step I: 1-((E)-3-{4-[3-(3,5-difluorophenyl)-4-methyl-7-(tetrahydropyran-2-yloxy)-2H-chromen-2-yl]-phenyl}allyl)-4-fluoromethylpiperidine

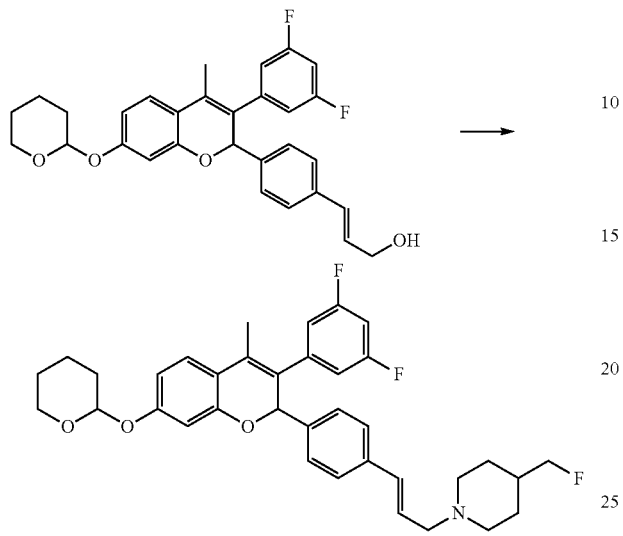

A solution of methanesulfonyl chloride (0.11 mL, 1.4 mmol) in dichloromethane (1 mL) was added drop-wise to a stirred solution of (E)-3-{4-[3-(3,5-difluorophenyl)-4-methyl-7-(tetrahydropyran-2-yloxy)-2H-chromen-2-yl] phenyl}prop-2-en-1-ol (0.57 g, 1.17 mmol) and triethylamine (0.24 mL, 1.75 mmol) in dichloromethane (5 mL) at 0-5° C. The reaction mixture was further stirred at 0-5° C. for 30 minutes. Water was added to the reaction mixture and the organic layer was separated. The aqueous layer was extracted with dichloromethane. The combined organic layer was dried over anhydrous sodium sulfate and used for the next step. This solution was added to a solution of triethylamine (0.65 mL, 4.7 mmol) and 4-fluoromethylpiperidine hydrochloride (0.54 g, 3.5 mmol) in acetonitrile (6 mL) at 0-5° C. The reaction mixture was stirred at room temperature for 1.5 hours. Water was added and the mixture was extracted with dichloromethane. The combined organic layer was dried over anhydrous sodium sulfate and concentrated under reduced pressure to get a crude mass which was purified by column chromatography (silica gel, methanol:dichloromethane (5:95)) to yield the title compound.

Step II: 3-(3,5-difluorophenyl)-2-{4-[(E)-3-(4-fluoromethylpiperidin-1-yl)propenyl]phenyl}-4-methyl-2H-chromen-7-ol (Compound 3)

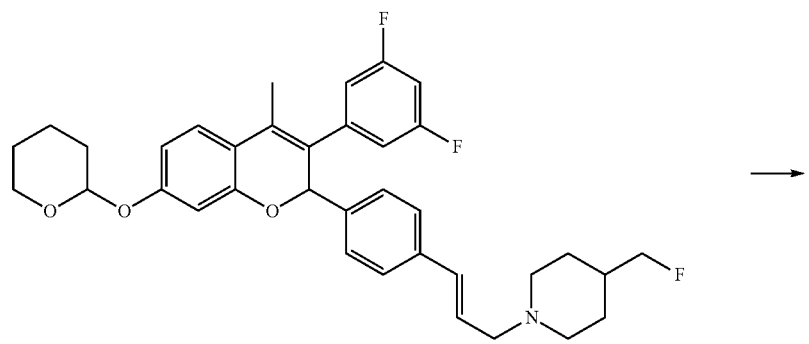

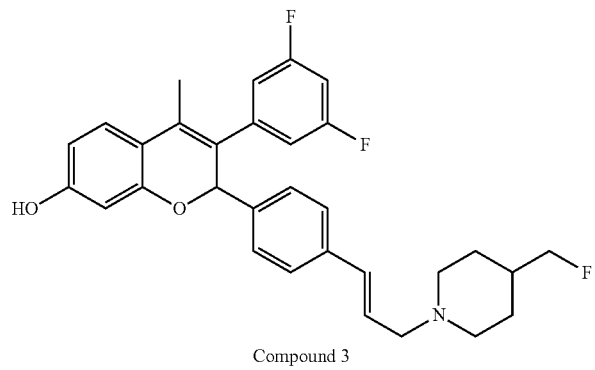

Compound 3

A solution of 1-((E)-3-{4-[3-(3,5-difluorophenyl)-4-methyl-7-(tetrahydropyran-2-yloxy)-2H-chromen-2-yl]-phenyl}allyl)-4-fluoromethylpiperidine (0.7 g, 1.18 mmol) in a mixture of sulfuric acid (0.07 mL) and methanol (5 mL) was stirred at room temperature for 10 minutes. The reaction mixture was made alkaline with a saturated solution of sodium bicarbonate and extracted with dichloromethane. The combined organic layer was dried over anhydrous sodium sulfate and concentrated under reduced pressure to get a crude mass which was purified by column chromatography (silica gel, methanol:dichloromethane (8:92)) to get the title compound.

Example 5: Preparation of 3-(3,5-difluorophenyl)-2-[4-[(E)-3-[(3R)-3-(fluoromethyl)pyrrolidin-1-yl]prop-1-enyl]phenyl]-4-methyl-2H-chromen-7-ol (Compound 4)

Compound 4

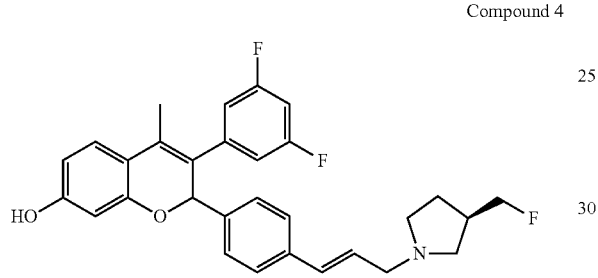

The compound 4 was prepared following an analogous process of Example 4 by using (3R)-3-(fluoromethyl)pyrrolidine hydrochloride instead of 4-fluoromethylpiperidine hydrochloride in step-I.

Example 6: Preparation of 3-(3,5-difluorophenyl)-4-methyl-2-[4-[(E)-3-[(3R)-3-methylpyrrolidin-1-yl]prop-1-enyl]phenyl]-2H-chromen-7-ol (Compound 5)

Compound 5

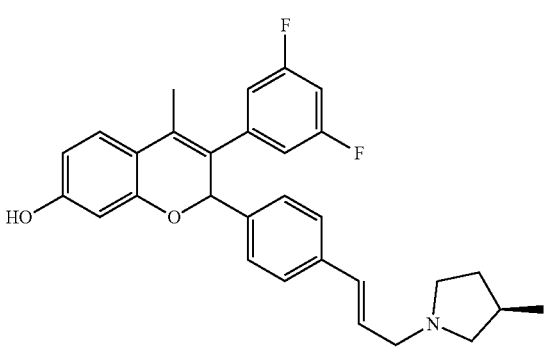

The compound 5 was prepared by following an analogous process of Example 4 by using (3R)-3-methylpyrrolidine hydrochloride instead of 4-fluoromethylpiperidine hydrochloride in step-I.

Example 7: Preparation of 3-(3,5-difluorophenyl)-2-{4-[(Z)-3-(3-fluoromethylazetidin-1-yl)propenyl]phenyl}-4-methyl-2H-chromen-7-ol (Compound 6)

Compound 6

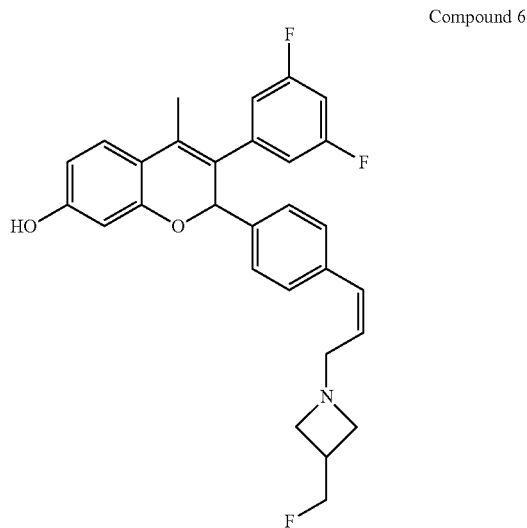 [SMILES: CC1=C(c2cc(F)cc(F)c2)C(c2ccc(/C=C\CN3CC(CF)C3)cc2)Oc2cc(O)ccc21]

Step I: 3-[4-[3-(3,5-difluorophenyl)-4-methyl-7-tetrahydropyran-2-yloxy-2H-chromen-2-yl]phenyl]prop-2-yn-1-ol

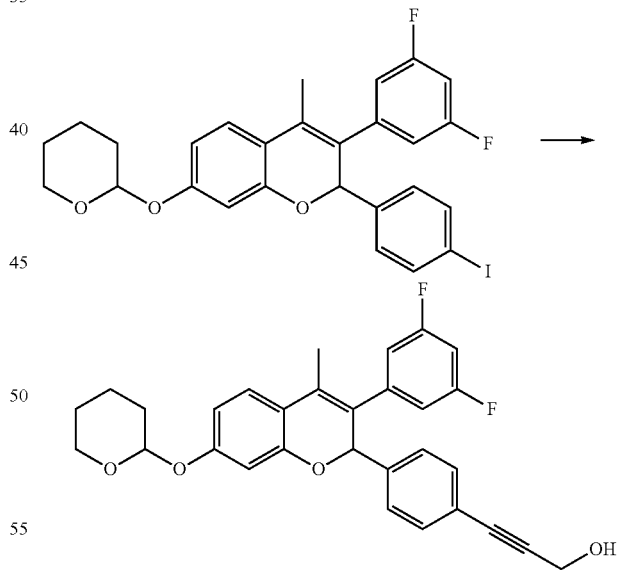

Bis(triphenylphosphine)palladium(II) dichloride (0.125 g, 0.18 mmol) was added to a stirred solution of 3-(3,5-difluorophenyl)-2-(4-iodophenyl)-4-methyl-7-tetrahydropyran-2-yloxy-2H-chromene (2.0 g, 3.6 mmol), propargyl alcohol (0.60 g, 10.7 mmol) and cuprous(I) iodide (0.054 g, 0.29 mmol) in a mixture of tetrahydrofran:triethylamine (1:1, 64 mL). Stirring was continued at room temperature for 2 hours. The reaction mixture was concentrated under reduced pressure to get a crude residue which was purified by column chromatography (silica gel, toluene-ethyl acetate (4:1)) to yield the title compound.

Step II: 1-[3-[4-[3-(3,5-difluorophenyl)-4-methyl-7-tetrahydropyran-2-yloxy-2H-chromen-2-yl]phenyl]prop-2-ynyl]-3-(fluoromethyl)azetidine

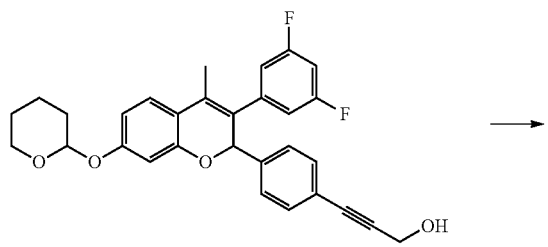

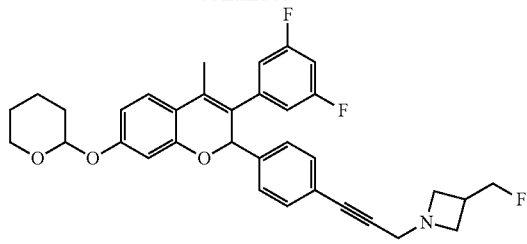

The step II compound was prepared by following an analogous process of Example 4, step-I.

Step III: 1-[(Z)-3-[4-[3-(3,5-difluorophenyl)-4-methyl-7-tetrahydropyran-2-yloxy-2H-chromen-2-yl]phenyl]allyl]-3-(fluoromethyl)azetidine

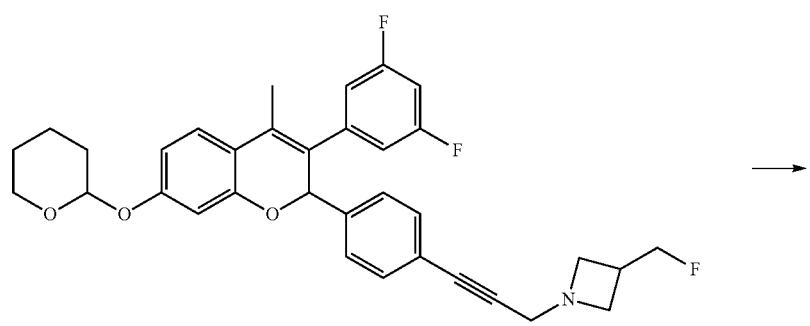

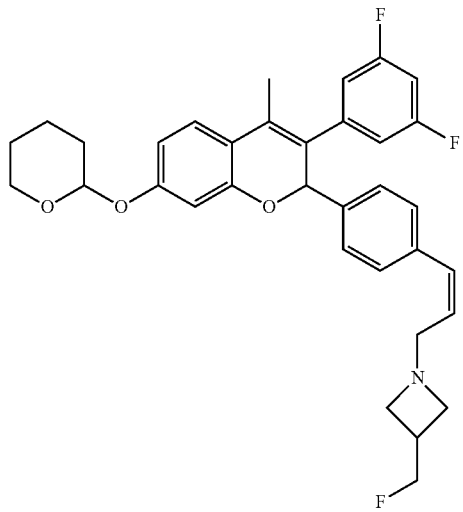

Lindlar catalyst (0.125 g, 25% w/w) was added to a solution of 1-[3-[4-[3-(3,5-difluorophenyl)-4-methyl-7-tetrahydropyran-2-yloxy-2H-chromen-2-yl]phenyl] prop-2-ynyl]-3-(fluoromethyl)azetidine (0.50 g, 0.89 mmol) and quinoline (0.05 g, 10% w/w) in ethanol (10 mL). The reaction mixture was stirred under hydrogen atmosphere using a hydrogen gas filled balloon at room temperature for 5 hours. The reaction mixture was filtered and washed with ethanol. The filtrate was concentrated under reduced pressure to get a crude mass which was purified by column chromatography (silica gel, dichloromethane:methanol (97:3)) to yield the title compound.

Step IV: 3-(3,5-difluorophenyl)-2-{4-[(Z)-3-(3-fluoromethylazetidin-1-yl)propenyl]phenyl}-4-methyl-2H-chromen-7-ol (Compound 6)

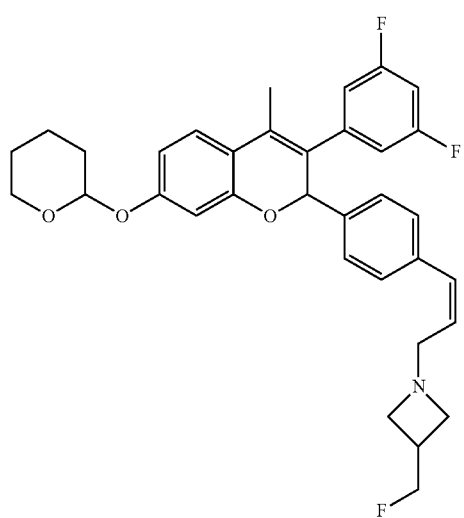

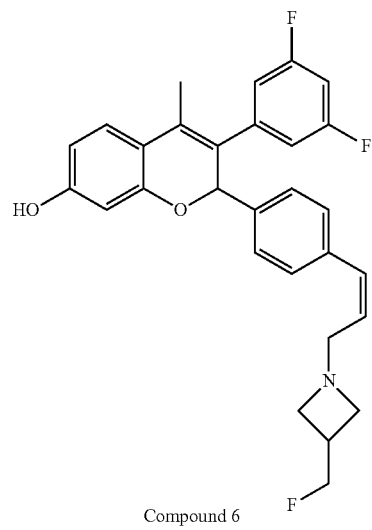

Compound 6

THP protection was removed using an analogous process of Example 4 (step II) to obtain the racemic Compound 6.

Example 8: Preparation of 3-(3,5-difluorophenyl)-2-[4-[3-[3-(fluoromethyl) azetidin-1-yl]prop-1-ynyl] phenyl]-4-methyl-2H-chromen-7-ol (Compound 7)

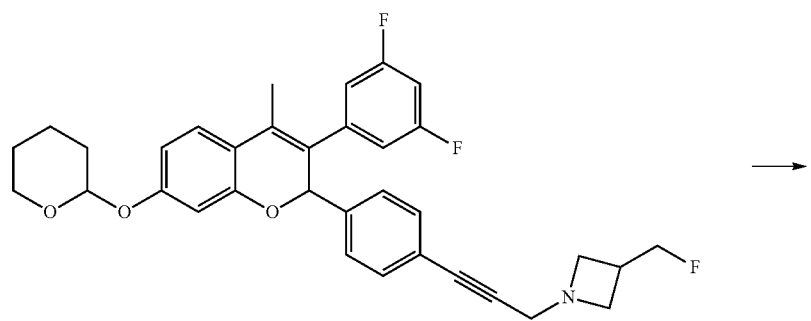

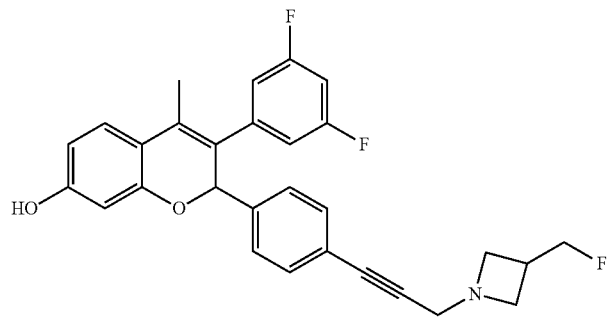

Compound 7

The racemic compound 7 was prepared by removing the THP protection of the Example 7 (step II) compound using an analogous process of Example 4, step II.

The H NMR data of compounds of Formula I, Formula Ia, and related analogues are provided below:

| Compound | Chirality# | Structure/Chemical Name | $^1$H NMR data |
|---|---|---|---|
| Formula I | Racemic | Formula I<br>3-(3,5-Difluorophenyl)-2-[4-[(E)-3-[3-(fluoromethyl)azetidin-1-yl]prop-1-enyl]phenyl]-4-methyl-2H-chromen-7-ol | (DMSO-d$_6$, 500 MHz); 2.12 (s, 3H); 3.10-3.23 (m, 1H); 3.89-4.00 (m, 4H); 4.15 (t, J = 10.52 Hz, 2H); 4.55 (d, J = 4.68 Hz, 1H); 4.67 (d, J = 4.68 Hz, 1H); 6.12-6.23 (m, 3H); 6.43 (dd, J$_1$ = 8.44 Hz, J$_2$ = 2.44 Hz, 1H); 6.80 (d, J = 15.97 Hz, 1H); 7.06-7.20 (m, 3H); 7.25 (d, J = 8.44 Hz, 1H); 7.36 (d, J = 8.28 Hz, 2H); 7.43 (d, J = 8.28 Hz, 2H); one exchangeable proton. |
| Formula Ia | S | Formula Ia<br>(2S)-3-(3,5-Difluorophenyl)-2-[4-[(E)-3-[3-(fluoromethyl)azetidin-1-yl]prop-1-enyl]phenyl]-4-methyl-2H-chromen-7-ol | (DMSO-d$_6$, 500 MHz); 2.12 (s, 3H); 2.73-2.85 (m, 1H); 3.05 (t, J = 6.65 Hz, 2H); 3.21 (d, J = 5.50 Hz, 2H); 3.36 (t, J = 7.25 Hz, 2H); 4.51 (d, J = 6.05 Hz, 1H); 4.60 (d, J = 5.80 Hz, 1H); 6.11 (s, 1H); 6.14-6.21 (m, 2H); 6.43 (dd, J$_1$ = 8.40 Hz, J$_2$ = 2.40 Hz, 1H); 6.50 (d, J = 15.95 Hz, 1H); 7.04-7.09 (m, 2H); 7.11-7.17 (m, 1H); 7.24 (d, J = 7.24 Hz, 1H); 7.29 (d, J = 8.25 Hz, 2H); 7.35 (d, J = 8.25 Hz, 2H); one exchangeable proton. |
| Formula Ib | R | Formula Ib<br>(2R)-3-(3,5-Difluorophenyl)-2-[4-[(E)-3-[3-(fluoromethyl)azetidin-1-yl]prop-1-enyl]phenyl]-4-methyl-2H-chromen-7-ol | (DMSO-d$_6$, 500 MEz); 2.12 (s, 3H); 2.73-2.84 (m, 1H); 3.03 (t, J = 6.65 Hz, 2H); 3.20 (d, J = 5.60 Hz, 2H); 3.35 (t, J = 7.30 Hz, 2H); 4.51 (d, J = 6.10 Hz, 1H); 4.60 (d, J = 6.10 Hz, 1H); 6.11 (s, 1H); 6.14-6.21 (m, 2H); 6.43 (dd, J$_1$ = 8.40 Hz, J$_2$ = 2.35 Hz, 1H); 6.50 (d, J = 16.00 Hz, 1H); 7.04-7.10 (m, 2H); 7.11-7.17 (m, 1H); 7.24 (d, J = 8.45 Hz, 1H); 7.29 (d, J = 8.25 Hz, 2H); 7.35 (d, J = 8.20 Hz, 2H); one exchangeable proton. |

| Compound | Chirality# | Structure/Chemical Name | 1H NMR data |
|---|---|---|---|
| Compound 2 | Racemic | 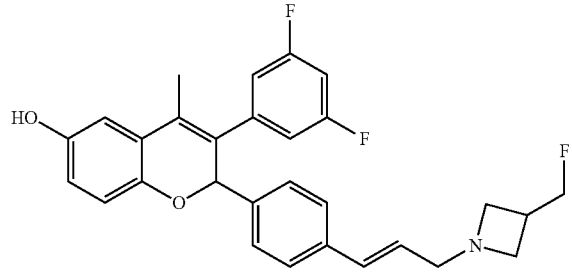 [SMILES: CC1=C(c2cc(F)cc(F)c2)C(c2ccc(/C=C/CN3CC(CF)C3)cc2)Oc2ccc(O)cc21]<br>Compound 2<br>3-(3,5-Difluorophenyl)-2-[4-[(E)-3-[3-(fluoromethyl)azetidin-1-yl]prop-1-enyl]phenyl]-4-methyl-2H-chromen-6-ol | (DMSO-$d_6$, 500 MHz); 2.12 (s, 3H); 2.78-2.91 (br m, 1H); 3.14-3.25 (m, 2H); 3.28-3.38 (m, 2H); 3.45-3.58 (m, 2H); 4.49 (d, J = 6.00 Hz, 1H); 4.61 (d, J = 5.96 Hz, 1H); 6.10 (s, 1H); 6.19 (dt, $J_1$ = 12.44 Hz, $J_2$ = 3.60 Hz, 1H); 6.50-6.60 (br m, 3H); 6.81-6.86 (m, 1H); 7.02-7.23 (m, 3H); 7.25-7.32 (m, 2H); 7.34-7.38 (m, 2H); one exchangeable proton. |
| Compound 3 | Racemic | 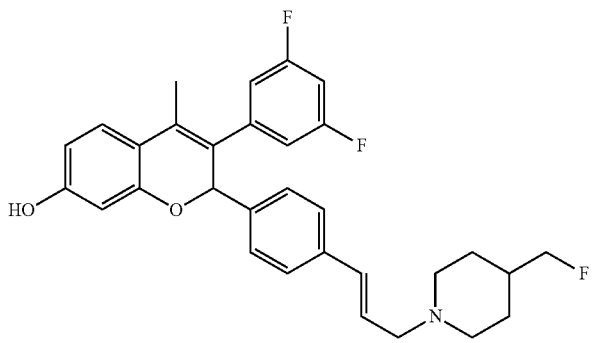 [SMILES: CC1=C(c2cc(F)cc(F)c2)C(c2ccc(/C=C/CN3CCC(CF)CC3)cc2)Oc2cc(O)ccc21]<br>Compound 3<br>3-(3,5-Difluorophenyl)-2-{4-[(E)-3-(4-fluoromethyl piperidin-1-yl)propenyl]phenyl}-4-methyl-2H-chromen-7-ol | (DMSO-$d_6$, 500 MHz); 1.25-1.29 (m, 2H), 1.65 (d, J = 11.3 Hz, 3H), 1.91-1.96 (m, 2H), 2.12 (s, 3H), 2.91 (d, J = 11.1 Hz, 2H), 3.1 (d, J = 6.4 Hz, 2H), 4.26 (d, J = 5.5 Hz), 1H), 4.35 (d, J = 5.7 Hz, 1H), 6.13 (br s, 1H), 6.17 (d, J = 2.3 Hz, 1H), 6.26-6.32 (m, 1H), 6.42 (dd, $J_1$ = 8.4 Hz, $J_2$ = 2.3 Hz, 1H), 6.48 (d, J = 15.9 Hz, 1H), 7.11 (d, J = 6.7 Hz, 2H), 7.18 (dt, $J_1$ = 18.7 Hz, $J_2$ = 9.4 Hz, 1H), 7.24 (d, J = 8.5 Hz, 1H), 7.29 (d, J = 8.2 Hz, 2H), 7.37 (d, J = 8.2 Hz, 2H), 9.7 (s, 1H). |
| Compound 4 | Racemic | 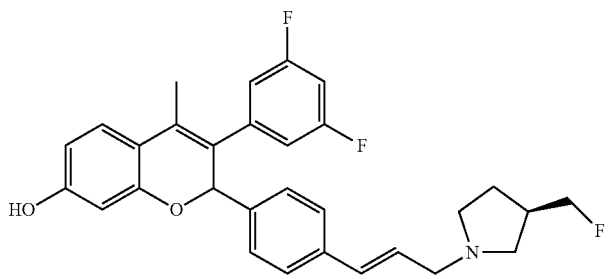 [SMILES: CC1=C(c2cc(F)cc(F)c2)C(c2ccc(/C=C/CN3CC[C@@H](CF)C3)cc2)Oc2cc(O)ccc21]<br>Compound 4<br>3-(3,5-Difluorophenyl)-2-[4-[(E)-3-[(3R)-3-(fluoromethyl)pyrrolidin-1-yl]prop-1-enyl]phenyl]-4-methyl-2H-chromen-7-ol | (DMSO-$d_6$, 500 MHz); 1.4-1.49 (m, 1H); 1.82-1.93 (m, 1H); 2.12 (s, 3H); 2.32-2.4 (m, 1H); 2.4-2.5 (m, 2H); 2.5 (m, 2H); 3.2 (d, J = 6.29 Hz, 1H); 4.28 (d, J = 6.29 Hz, 1H); 4.38 (d, J = 6.36 Hz, 1H); 6.14 (s, 1H); 6.17 (d, J = 2.31 Hz, 1H); 6.3 (dt, $J_1$ = 15.8 Hz, $J_2$ = 6.42 Hz, 1H); 6.41 (dd, $J_1$ = 8.41 Hz, $J_2$ = 2.3 Hz, 1H); 6.5 (d, J = 15.9 Hz, 1H); 7.09 (br d, 2H); 7.15-7.21 (m, 1H); 7.24 (d, J = 8.43 Hz, 1H); 7.29 (d, J = 8.17 Hz, 2H); 7.37 (d, J = 8.2 Hz, 2H); two protons were merged with dmso. |

-continued

| Compound | Chirality[#] | Structure/Chemical Name | $^1$H NMR data |
|---|---|---|---|
| Compound 5 | Racemic | 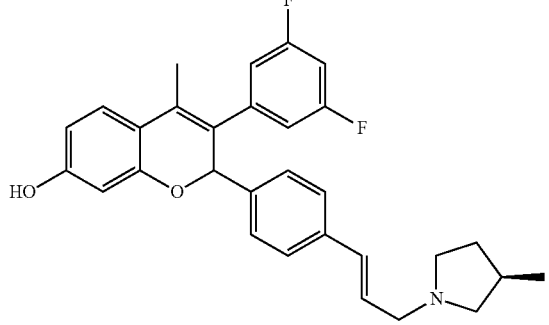

Compound 5
3-(3,5-Difluorophenyl)-4-methyl-2-[4-[(E)-3-[(3R)-3-methylpyrrolidin-1-yl]prop-1-enyl]phenyl]-2H-chromen-7-ol | (DMSO-d$_6$, 500 MHz); 1.06 (d, J = 6.75 Hz, 3H); 1.40-1.50 (m, 1H); 2.02-2.10 (m, 1H); 2.12 (s, 3H); 2.24-2.36 (m, 1H); 2.40-2.48 (m, 1H); 2.90-2.98 (m, 2H); 3.11 (dd, J$_1$ = 9.90 Hz, J$_2$ = 7.60 Hz, 1H); 3.55 (d, J = 6.75 Hz, 2H); 6.13 (s, 1H); 6.20 (d, J = 2.35 Hz, 1H); 6.33 (dt, J$_1$ = 15.85 Hz, J$_2$ = 6.80 Hz, 1H); 6.44 (dd, J$_1$ = 8.40 Hz, J$_2$ = 2.40 Hz, 1H); 6.66 (d, J = 15.85 Hz, 1H); 7.04-7.18 (m, 3H); 7.25 (d, J = 8.45 Hz, 1H); 7.33 (d, J = 8.20 Hz, 2H); 7.40 (d, J = 8.20 Hz, 2H); one exchangeable proton. |
| Compound 6 | Racemic | 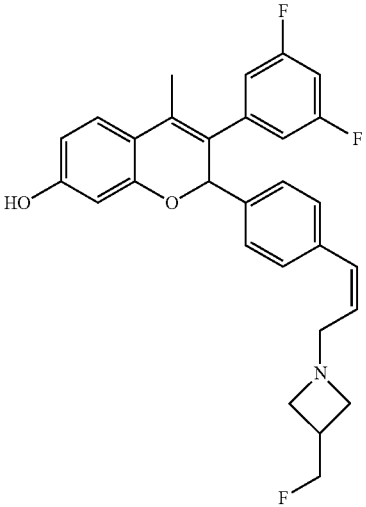 [SMILES: CC1=C(c2cc(F)cc(F)c2)C(c2ccc(/C=C\CN3CC(CF)C3)cc2)Oc2cc(O)ccc21]

Compound 6
3-(3,5-Difluorophenyl)-2-{4-[(Z)-3-(3-fluoromethylazetidin-1-yl)propenyl]phenyl}-4-methyl-2H-chromen-7-ol | (DMSO-d$_6$, 500 MHz); 2.13 (s, 3H); 2.7-2.9 (m, 1H); 3.02 (t, J = 6.5 Hz, 2H); 3.3-3.4 (m, 4H); 4.47 (d, J = 6.18 Hz, 1H); 4.57 (d, J = 6.17 Hz, 1H); 5.58 (dt, J$_1$ = 12.11 Hz, J$_2$ = 6.2 Hz, 1H); 6.17 (s, 1H); 6.20 (d, J = 2.39 Hz, 1H); 6.43 (dd, J$_1$ = 8.44 Hz, J$_2$ = 2.41 Hz, 2H); 7.1-7.15 (m, 2H); 7.16-7.27 (br, 4H); 7.35 (d, J = 8.2 Hz, 2H); one exchangeable proton. |
| Compound 7 | Racemic | 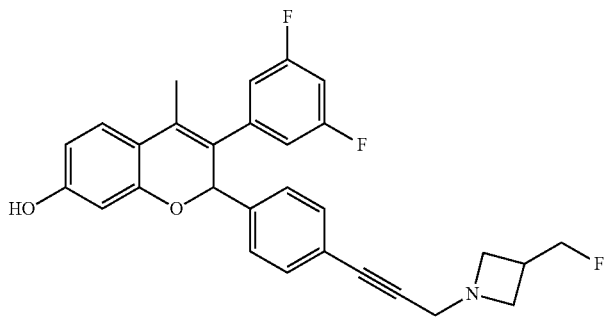 [SMILES: CC1=C(c2cc(F)cc(F)c2)C(c2ccc(C#CCN3CC(CF)C3)cc2)Oc2cc(O)ccc21]

Compound 7
3-(3,5-Difluorophenyl)-2-[4-[3-[3-(fluoromethyl)azetidin-1-yl]prop-1-ynyl]phenyl]-4-methyl-2H-chromen-7-ol | (DMSO-d$_6$, 500 MHz); 2.11 (s, 3H); 2.73-2.82 (m, 1H); 3.17 (t, J = 6.76 Hz, 2H); 3.41 (t, J = 7.51 Hz, 2H); 3.49 (s, 2H); 4.50 (d, J = 6.14 Hz, 1H); 4.60 (d, J = 6.14 Hz, 1H); 6.1-6.2 (m, 2H); 6.43 (d, J = 2.2 Hz, 1H); 7.08-7.14 (br, 2H); 7.14-7.20 (m, 1H); 7.24 (d, J = 8.44 Hz, 1H); 7.34 (d, J = 8.1 Hz, 2H); 7.40 (d, J = 8.1 Hz, 2H), one exchangeable proton. |

[#]Chirality at 2$^{nd}$ position of 2H-chromene ring.

The biological activities of the compounds of the present disclosure was determined via the following assays:

Selective Estrogen Receptor Degradation (SERD) Assay:

The SERD activity for the test compounds was evaluated in MCF-7 cells harboring ER wild type, and MCF-7 cells harboring mutant ER (WT/D538G and WT/Y537S). Briefly, cells were plated in phenol red free RPMI1640 medium supplemented with 5% charcoal stripped fetal bovine serum. The seeding density was 40000 cells/well for MCF-7 WT and MCF-7 D538G and 50000 cells/well MCF-7 Y537S in a 48-well plate. Following overnight incubation, the cells were treated with varying concentrations of test compounds (final concentration: 1000 nM to 0.01 nM, 0.1% DMSO) for 4 days. The cells were lysed using PBS supplemented with 1 mM EDTA, 0.5% Triton X-100, 5 mM NaF, 6 M urea, and 1× Protease inhibitor cocktail. The lysate was analyzed for ER alpha protein using western blot. For the western blot, the cell lysate (12.5-40 μg total protein) was resolved on a 10% SDS PAGE and transferred onto a PVDF membrane. The blots were blocked using 5% skim milk powder in 0.1% PBS-T for 1 hour at room temperature, followed by co-incubation with rabbit anti-human β-actin antibody and rabbit anti-human ERα antibody for 2 hours at room temperature. The blots were subsequently probed with anti-rabbit IgG-HRP conjugate as secondary antibody for 1 hour at room temperature. The blots were developed by using West Pico Super Signal Chemiluminescence substrate and the bands were processed for densitometry analysis using Image Lab software (BioRad version 6.0.0). ERα band intensity was normalized to that housekeeping protein for respective samples. The % ER remaining was calculated by normalizing against the vehicle control (as 100%).

MCF-7 Cell Growth Inhibition Assay:

The anti-proliferative activity of the test compounds were evaluated in a growth inhibition assay. Briefly, MCF-7 cells harboring ER wild type (Wt), and MCF-7 cells harboring mutant ER (WT/D538G and WT/Y537S) were seeded at a density of 1000 cells/well in 96-well plate in phenol red free RPMI1640 medium supplemented with 10% charcoal stripped fetal bovine serum. The cells were incubated overnight at 37° C. and 5% $CO_2$ followed by the addition of varying concentrations of the test compounds in DMSO. Final concentration of DMSO in the well was 0.5%. Following a seven-day incubation of cells with the test compounds, cell viability was assessed using a Prestoblue™ reagent. The percent inhibition of cell proliferation was calculated by normalizing the cell viability using a vehicle control as 0% inhibition of proliferation.

The result of the ER-α degradation assay of the compound of Formula I and its closely related compounds at 1 nM concentration was as shown below in Table 1.

TABLE 1

ER-α degradation assay

| Compound | % of ER-α remaining at 1 nM |
|---|---|
| Formula I | 41 |
| Compound 2 | 100 |
| Compound 3 | 100 |
| Compound 4 | 100 |
| Compound 5 | 85 |
| Compound 6 | 80.8 |
| Compound 7 | 100 |

As apparent from the table above, the compound of Formula I showed significantly more ER-α degradation in MCF-7 cell line (Wt type) as compared to structurally close compounds including its regioisomer Compound 2. It was surprisingly found that changing the position of hydroxyl group in the compound of Formula I from the $7^{th}$ position to the $6^{th}$ position on the chromene moiety, as in Compound 2, led to the complete loss of the SERD activity. Compounds 3, 4, and 5, which have either 6- or 5-membered heterocycloalkyl rings in the side chain had negligible SERD activity (more than 80% of ER remaining), whereas the compound of Formula I which has a 4-membered azetidine ring in the side chain showed good degradation of ER (only about 41% of ER remaining). It was also surprisingly found that changing the double bond in the side chain of the compound of Formula I to a triple bond as in Compound 7 led to complete loss of SERD activity. Moreover, Compound 6, which is geometric isomer (Cis-isomer) of a compound of Formula I, showed very negligible SERD activity.

Thus, the compound of Formula I has all the optimum structural attributes required for a potent selective estrogen receptor degrader. The inventors of the present invention further resolved the compound of Formula I into its S and R stereoisomers. The S isomer is presented as Formula Ia and the R isomer is presented as Formula Ib in the current disclosure.

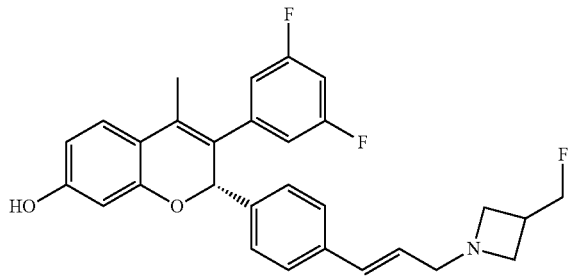

Compound Ia

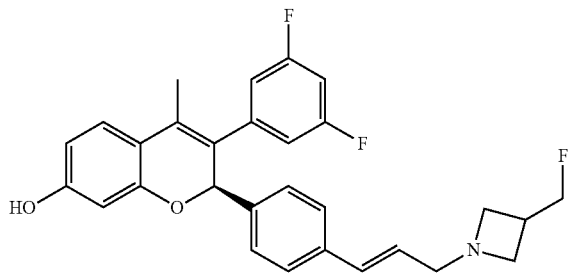

Compound Ib

The compound of Formula Ia and compound of Formula Ib were further tested for their anti-proliferative activity in growth inhibition assay (MCF-7 cell line) and for ER-α degradation. The results are provided as shown in Table 2 below:

TABLE 2

Comparison of in-vitro potency of compound of
Formula Ia with its R enantiomer, compound of Formula Ib

| | MCF-7 Growth Inhibition assay (IC$_{50}$; nM) | | | ER-α degradation assay | | | |
|---|---|---|---|---|---|---|---|
| | | | | Wt | | Y537S | D538G |
| Compound | Wt | Y537S | D538G | % of ER-α remaining at 1 nM | IC$_{50}$ (nM) | IC$_{50}$ (nM) | IC$_{50}$ (nM) |
| Formula Ia | 0.3 | 6.0 | 2.2 | 16.3 | 0.3 | 19.6 | 12.7 |
| Formula Ib | 69.9 | 1000 | 345.4 | 81.5 | 10.2 | (>1000) | (>1000) |

As evidenced from the table above, the compound of Formula Ia showed multifold superior activity over the compound of Formula Ib in MCF-7 growth inhibition assay (wild type), wherein the compound of Formula Ia is about 233 times more potent than compound of Formula Ib. The compound of Formula Ia also showed similar trends in a mutated cell line (Y537S & D538G). The compound of Formula Ia was also found to be multifold more potent in the ER-α degradation assay as compared to its R-enantiomer, wherein the compound of Formula Ia is about 34 times more potent than compound of Formula Ib in ER-α degradation (wild type). The R enantiomer has shown no ER-α degradation in mutated cell line (Y537S & D538G).

Pharmacokinetic Study:

In drug discovery it is very important to have good oral bioavailability and pharmacokinetic (PK) profile of the compound in order to become a good drug candidate for oral administration. Many compounds having potent in vitro efficacy fail to show therapeutic efficacy in human body. The lack of therapeutic efficacy of these compounds is mainly due to their inappropriate pharmacokinetic properties, such as low bioavailability, short half-life, rapid metabolism, or rapid clearance resulting in a short duration of action. Therefore a good drug candidate should have not only good potency, but also a good pharmacokinetic profile. The pharmacokinetic profile of the compounds of Formula Ia and Ib were determined as per the procedure provided below.

PK profiles were evaluated in female SD rats (n=2) following a single oral dose administration. Rats were fasted for 12-13 hours prior to dosing and feed was provided 2 hours after oral treatments. Dose formulations of compounds were prepared in Tween 80 (0.4% v/v of the total volume of suspension) in 0.5% carboxymethyl cellulose (CMC). Treatments were given at 50 mg/kg, p.o. To evaluate the plasma concentration, 0.2 mL blood was drawn from the rats through the retro-orbital plexus at 0.25, 1, 4, 8, 24, 48 and 72 hour time points post-treatment in Eppendorf tubes containing sodium heparin as an anticoagulant (100 IU/mL), and centrifuged immediately at 8500 rpm for 7 min at 4° C. Plasma was separated and stored at −70° C., until analysis. The analysis of samples was performed as per the method given below:

Working Calibration Standard and Quality Control Standards Preparation:

Working calibration standards were prepared having 0.10, 0.20, 2.00, 4.00, 8.00, 12.00, 16.00, and 20.00 µg/mL concentrations. Quality control standards were prepared at concentrations of 0.30, 3.00, 10.00, 15.00 and 60.00 µg/mL.

Preparation of Working Internal Standards (WIS):

Accurately weighed 5 mg of Carbamazepine was transferred into a 100 mL volumetric flask, dissolved and diluted up to the mark with diluent (0.1% formic acid in water: acetonitrile 30:70 v/v). A WIS of 5 µg/mL was prepared from the above solution.

Sample Processing:

5 µL of working standards and quality controls were spiked into 95 µL of blank plasma. 25 µl from the above spiked standards and quality controls were aliquoted into microcentrifuge tubes. 25 µL of study samples were also aliquoted into a micro centrifuge tube. 5 µL of WIS was added in zero standards to linearity and study samples except blank. The samples were further vortexed for 10-15 seconds. 150 µL of Milli Q water was added to all prepared samples and vortexed for 10-15 seconds. Samples were loaded on a preconditioned cartridge (preconditioning was done with 1 mL methanol followed by 1 mL Milli Q water). Cartridges were washed with 2×1 mL of Milli Q water. Elution was done with a 1 mL elution solution {acetonitrile: 0.1% formic acid solution (70:30)} in HPLC vials.

LC-MS/MS method:

Chromatographic separation was achieved on Chiral pack ID (250*4.6 mm, 5µ) with a flow rate of 1.25 mL/min with splitter and injection volume of 20 µL. The sample cooler was maintained at 10° C. The column oven temperature was set to 30° C. The mobile phase consisted of:

Mobile phase A: 1.47 g of ammonium bicarbonate into 1 L of water, 1 ml DEA, pH 9.2±0.1

Mobile phase B: methanol, wherein mobile phase A was mixed with mobile phase B in the ratio of 30:70 v/v, respectively. The retention time of the compound of Formula Ia, compound of Formula Ib and the internal standard were about 8.7, 7.6 and 4.2 min, respectively. The overall chromatographic run time was 16 minutes.

Detection was performed by tandem mass spectrometry (TSQ Quantum, Discovery MAX, Thermo Electron Corporation) and peak areas were integrated using LCquan software version 2.9 QF1. The detector was set on MRM mode where transition of 477.900 m/z→272.982 m/z (CE 20) was monitored for compound of Formula Ia or for compound of Formula Ib, and transition of 237.058 m/z→194.003 m/z (CE 16) was monitored for the internal standard.

The results of the pharmacokinetic study were as shown below in Table 3.

TABLE 3

PK Studies of compound of Formula Ia and Formula Ib

| | PK in rat at 50 mg/kg p.o. dose | | | | |
|---|---|---|---|---|---|
| Compound | Tmax (h) | C$_{max}$ (ng/mL) | AUC$_{last}$ (hr*ng/mL) | AUC$_{inf\_obs}$ (hr*ng/mL) | T$_{1/2}$ (h) |
| Formula Ia | 4.00 | 343 | 7582 | 9804 | 26 |
| Formula Ib | 4.00 | 119 | 1795 | 2356 | 10 |

As apparent from above table, compound of Formula Ia showed a superior pharmacokinetic profile when compared to its R-enantiomer. The C$_{max}$ of the compound of Formula Ia was found to be about 2.9 fold greater than that of the compound of Formula Ib. Similarly the $AUC_{last}$ of the compound of Formula Ia was found to be about 4.2 fold greater than that of the compound of Formula Ib.

In-Vivo Efficacy of Compound of Formula I and Compound of Formula Ia:

The efficacy of the compound of Formula I and the compound of Formula Ia were evaluated in female athymic nude mice harboring subcutaneous MCF7-Y537S xenografts. Dose formulations of the compound of Formula I and the compound of Formula Ia were prepared in Tween 80 (0.4% v/v of the total volume of suspension) in 0.5% w/v carboxymethylcellulose (CMC) and administered once daily orally for 28 days. Two perpendicular diameters of tumor were measured with digital Vernier caliper. Tumor volume (V) was calculated using the following equation: $V=(a^2 \times b)/2$, where "a" is the width of the tumor (small diameter), and "b" the length (large diameter), both in millimeters. Tumors were monitored twice weekly and compared with a vehicle treated group. The results of the study were as shown below in Table 4. Both the compounds, of Formula Ia and of Formula I, showed significant reduction in the tumor growth when compared to the vehicle group (see FIG. 1). The results showed that compound of Formula Ia at 50 mg/kg and the racemic compound of Formula I at 100 mg/kg dose levels showed similar tumor growth inhibition (TGI) as compared to the vehicle group with 56% and 57% TGI, respectively.

TABLE 4

In-vivo efficacy of compound of Formula Ia and compound of Formula I in MCF7-Y537S mice xenografts

| # | Dose | % Tumor growth inhibition compared to vehicle group after 28 days |
| --- | --- | --- |
| Formula Ia | 50 mg/kg, p.o., 28 days | 56 |
| Formula I | 50 mg/kg, p.o., 28 days | 46 |
| Formula I | 100 mg/kg, p.o., 28 days | 57 |

In summary, the compounds of the present disclosure showed better potency in in-vitro assays, for example in an. ER-α degradation assay, than their closely related compounds. The compounds of present disclosure also showed good in-vivo efficacy in an MCF7-Y537S xenograft. The compounds of the present disclosure, particularly the compound of Formula Ia, showed a good pharmacokinetic profile and thus can be suitable for oral administration. The compounds of the present disclosure or their pharmaceutically acceptable salts can be formulated in oral dosage forms and can be used for the treatment of diseases which are related to modulation of ERs, such as ER-positive breast cancer.

What is claimed is:

1. A compound 3-(3,5-difluorophenyl)-2-[4-[(E)-3-[3-(fluoromethyl)azetidin-1-yl]prop-1-enyl]phenyl]-4-methyl-2H-chromen-7-ol represented by Formula I:

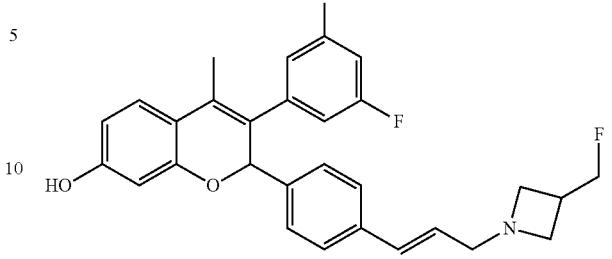

Formula I or a pharmaceutically acceptable salt thereof.

2. A compound (2S)-3-(3,5-difluorophenyl)-2-[4-[(E)-3-[3-(fluoromethyl)azetidin-1-yl]prop-1-enyl]phenyl]-4-methyl-2H-chromen-7-ol represented by Formula Ia:

Formula Ia or a pharmaceutically acceptable salt thereof.

3. The compound of claim 2, wherein the enantiomeric ratio of the compound of Formula Ia is greater than 75:25, greater than 80:20, greater than 85:15, greater than 90:10, greater than 95:5, greater than 99:1 or is 100:0.

4. A pharmaceutical composition comprising a compound of claim 1 and a pharmaceutically acceptable carrier, diluent, or excipient.

5. A pharmaceutical composition comprising a compound of claim 2 and a pharmaceutically acceptable carrier, diluent, or excipient.

6. A composition comprising the compound of claim 2 and a, compound of Formula Ib Formula Ib wherrein a content of the compound of Formula Ib is less than 25%, less than 20%, less than 15%, less than 10%, less than 5%, less than 1%, less than 0.5%, less than 0.1, less than 0.05%, less than 0.01% w/w or absent with respect to the compound of Formula Ia.

7. The pharmaceutical composition of claim 4, wherein an amount of S-enantiomer of Formula I present in the composition is at least 75% of a total amount of enantiomers of Formula I present in the composition.

8. The pharmaceutical composition of claim 7, wherein the amount of S-enantiomer of Formula I present in the composition is at least 99% of the total amount of enantiomers of Formula I present in the composition.

9. The pharmaceutical composition of claim 8, wherein the amount of S-enantiomer of Formula I present in the composition is 100% of the total amount of enantiomers of Formula I present in the composition.

10. A method of treatment of a cancer in a human being, the method comprising administering an effective amount of the compound of claim 1 to a human in need thereof, wherein the cancer is selected from the group consisting of ER-mediated breast cancer, ER-mediated endometrial cancer, ER-mediated brain cancer, and ER-mediated ovary cancer.

11. The method of treatment of claim 10, wherein the cancer is ER-mediated breast cancer.

12. A method of treatment of a cancer in a human being, the method comprising administering an effective amount of the compound of claim 2 to a human in need thereof, wherein the cancer is selected from the group consisting of ER-mediated breast cancer, ER-mediated endometrial cancer, ER-mediated brain cancer, and ER-mediated ovary cancer.

13. The method of treatment of claim 12, wherein the cancer is ER-mediated breast cancer.

* * * * *